(12) United States Patent
Travis et al.

(10) Patent No.: US 8,846,899 B2
(45) Date of Patent: Sep. 30, 2014

(54) MALTOSIDE AND PHOSPHOCHOLINE DERIVATIVES, USES THEREOF AND METHODS OF PREPARING ARTIFICIAL LIPID STRUCTURES THEREOF

(75) Inventors: Benjamin R. Travis, Maumee, OH (US); Ritesh Mittal, Sylvania, OH (US); Lijun Huang, Waterville, OH (US); Liang Tang, Waterville, OH (US)

(73) Assignee: Anatrace Products, LLC, Maumee, OH (US)

( * ) Notice: Subject to any disclaimer, the term of this patent is extended or adjusted under 35 U.S.C. 154(b) by 53 days.

(21) Appl. No.: 13/272,090

(22) Filed: Oct. 12, 2011

(65) Prior Publication Data

US 2013/0096295 A1 Apr. 18, 2013

(51) Int. Cl.
C07D 249/04 (2006.01)
C07H 3/04 (2006.01)
C07H 5/04 (2006.01)
C07F 9/10 (2006.01)
C07H 15/26 (2006.01)
C07F 9/6518 (2006.01)

(52) U.S. Cl.
CPC ............ C07F 9/65182 (2013.01); C07H 15/26 (2013.01); C07F 9/103 (2013.01)
USPC ........... 536/55.1; 536/123.1; 548/255; 552/3; 558/6; 558/166

(58) Field of Classification Search
USPC .................. 536/55.1, 123.13; 548/255; 552/3; 558/166, 6
See application file for complete search history.

(56) References Cited

U.S. PATENT DOCUMENTS

| 5,851,536 | A * | 12/1998 | Yager et al. .................... 424/400 |
| 7,375,234 | B2 | 5/2008 | Sharpless et al. |
| 7,618,944 | B2 | 11/2009 | Breitenkamp et al. |
| 7,709,655 | B2 | 5/2010 | Zhang |
| 7,763,736 | B2 | 7/2010 | Sharpless et al. |
| 2009/0156767 | A1* | 6/2009 | Emrick .......................... 526/171 |

OTHER PUBLICATIONS

Maheshwari et al, Macromol. Biosci. 2010, 10, 68-81.*
Lin et al, J. Org. Chem. 2010, 75, 4921-28.*
Ermeydan et al, New Journal of Chemistry, 2010, 34, 1153-62.*
O'Neil et al, Organic Letters, 2007, 9(2), 199-202.*
Lee et al, J. Poly. Sci. Part A, Polymer Chemistry, 2011, 49, 3163-73.*
Uzawa et al, Tetrahedron, 2005, 61, 5895-5905.*
Mosley et al, Biocatalysis and Biotransformation, Jan. 2010, 28(1), 41-50.*
Tagaki et al, J. Fluorine Chemistry, 2007, 128(2), 133-38.*
Affinity Photoprobes, LLC, "Biotinylated Photoaffinity Nucleotide Analogs," retrieved from http://photoprobe.com/lab/biotinphotoprobes.asp on May 11, 2010.
Alexander, J.P. and Cravatt, B.F., "Mechanism of Carbamate Inactivation of FAAH: Implications for the Design of Covalent Inhibitors and In Vivo Functional Probes for Enzymes," Chem Biol, Nov. 2005, vol. 12, No. 11, pp. 1179-1187.
Baseclick GMBH, Material Safety Data Sheet for Biotin-Azide, Product No. BCFA-003, Tutzing, Germany, May 1, 2009.
Chen, I-H.B. et al., "Nuclear envelope transmembrane proteins (NETs) that are up-regulated during myogenesis," BMC Cell Biology, 2006, vol. 7, p. 38.
Cobbold, C. et al., "Aberrant trafficking of transmembrane proteins in human disease," Trends in Cell Biology, Dec. 2003, vol. 13, No. 12, pp. 639-647.
Copland, M.J. et al., "Lipid based particulate formulations for the delivery of antigen," Immunology and Cell Biology, 2005, vol. 83, pp. 97-105.
Davis, S.S. et al., "Lipid Emulsions as Drug Delivery Systems," Annals of the New York Academy of Sciences, Dec. 1987, vol. 507, pp. 75-88.
Hegde, R.S. et al., A Transmembrane Form of the Prion Protein in Neurodegenerative Disease, Science, Feb. 6, 1998, vol. 279, pp. 827-834.
Jewett, J.C. et al., "Rapid Cu-Free Click Chemistry with Readily Synthesized Biarylazacyclooctynones," J Am Chem Soc, 2010, vol. 132, No. 11, pp. 3688-3690.
Kim, H.-Y.H. et al., "An Azido-Biotin Reagent for Use in the Isolation of Protein Adducts of Lipid-derived Electrophiles by Streptavidin Catch and Photorelease," Molecular & Cellular Proteomics, 2009, vol. 8, pp. 2080-2089.
Molecular Probes, Inc., "Click Chemistry Reagents," MP 10180, Aug. 5, 2009.
Nguyen, D.P. et al., "Genetic Encoding and Labeling of Aliphatic Azides and Alkynes in Recombinant Proteins via a Pyrrolysyl-tRNA Synthetase/tRNACUA Pair and Click Chemistry," J Am Chem Soc, 2009, vol. 131, No. 25, pp. 8720-8721.
Thermo Fisher Scientific, Inc., "Biotin-PEG3-Phosphine," retrieved from http://www.piercenet.com on May 11, 2010.
Thermo Fisher Scientific, Inc., "EZ-Link TFPA-PEG3-Biotin," retrieved from http://www.piercenet.com on May 11, 2010.

* cited by examiner

*Primary Examiner* — Ganapathy Krishnan
(74) *Attorney, Agent, or Firm* — Birch, Stewart, Kolasch & Birch, LLP

(57) ABSTRACT

Disclosed are saccharide and phosphocholine derivatives. The derivatives include azide and alkyne derivatives which form one end of a variable length carbon chain. The opposite end of the variable length carbon chain is covalently linked to the saccharide or phosphocholine. The saccharide may be, for instance, a maltoside. The alkyne and azide derivatives of the saccharides and phosphocholine may be reacted together to form amphiphilic molecules useful in cellular membrane studies and applications. By adjusting the length of the carbon chain, the biochemical and biophysical properties of the resultant 1,4-disubstituted 1,2,3-triazole compounds may be custom tailored for the intended application. Resultant molecules may form micelles, bicelle, lipid bilayers and other like structures useful in the isolation and purification of membrane bound or membrane associated proteins and biochemical components. The saccharides and phosphocholine molecules may be alternatively substituted as desired to provide additional flexibility in designing the desired end product.

18 Claims, 24 Drawing Sheets

MALTOSIDE AND PHOSPHOCHOLINE DERIVATIVES, USES THEREOF AND METHODS OF PREPARING ARTIFICIAL LIPID STRUCTURES THEREOF

FIELD OF THE INVENTION

Derivatives of maltosides and phosphocholine molecules are provided which may be applied in a variety of settings, including formation of lipid bilayers, micelles and bicelles, and which are useful in the study and purification of membrane-associated or membrane-bound proteins and other membrane components. The derivates may be azide derivatives and/or alkyne derivatives which allow formation of 1,4-disubstituted [1,2,3]-triazoles covalently linking, for instance, one molecule of maltoside derivative with one molecule of phosphocholine derivate. Derivatives may then be assembled into lipid structures providing expanded lipid-like environments for the isolation, purification and study of membrane-associated or membrane-bound proteins or other membrane components.

BACKGROUND OF THE INVENTION

The study of cellular membrane-associated proteins and membrane-bound proteins has been hampered by the need to provide unique microenvironments in which such proteins may exist naturally in the cell or as extracellular components. Much study and effort has been applied to this problem because the cellular components, upon isolation without membrane or lipid components to help solubilize them, form intractable and insoluble proteinaceous aggregates that precipitate out of solution in most simple aqueous environments. It has been found that such membrane proteins and components must not be isolated to absolute purity, but rather isolated such that they are transferred from the in vivo environment to an in vitro environment comprised of purified, synthetic lipids specially formulated and suited to provide the targeted protein or component with an physical and chemical environment much like that from which it is derived in vivo. The technique of purifying membrane proteins and components in the context of synthetic purified lipid or lipid-like molecules often provides useful quantities of such proteins and components for further characterization and use.

There exists several different families or classes of lipid or lipid-like molecules that help facilitate the purification and study of membrane proteins and components. In the past, purified preparations of naturally occurring lipids have been used, as well as synthetic lipids. Lipid-like molecules have also found much use in this field, including amphiphiles made of peptides and other chemical components which possess amphiphilic properties.

However, there still exists a great need for continued expansion of the field of membrane protein study to provide additional chemistries and lipid, or lipid-like, components to researchers, scientists, and industry for purifying proteins and components that, despite all available techniques, remain intractable and unable to be characterized because the proper chemistries and biochemistries have yet to be found which provide the exact unique microenvironment ideally suited for the isolation of those specific target proteins and/or component. To this end, the present inventors have endeavored to expand the field of membrane biology by finding and developing additional biochemical molecules having lipid-like characteristics which, when brought together under the proper conditions, form a multitude of different and expansive methodologies for the purification, isolation, and study of those membrane-associated or membrane-bound proteins and/or biochemical components which have thus far resisted purification or isolation and therefore, resisted further study.

Membrane-bound or membrane-associated proteins and/or biochemical components have been found to be highly useful in the study of human diseases and treatment thereof. Many neurological disorders may be traced directly to causalities that arise from mutations or other malfunctions, such as under-expression or over-expression, of membrane-bound or membrane-associated proteins or other biochemical components. Transmembrane proteins have been found to play crucial biological roles in intracellular communication and signaling, intracellular communication for instance between organelles and cytosol, ion transport, extracellular matrix interaction, tissue and arterial health and viral susceptibility. (See, for instance, Cobbold et al., "Aberrant trafficking of transmembrane proteins in human disease," *Trends Cell Biol.*, 13(12):639-647, 2003). Transmembrane proteins play key roles in diabetes, hypertension, depression, arthritis, cancer and neurological diseases such as cystic fibrosis. For instance cystic fibrosis has been tightly linked to the function of a transmembrane protein called Cystic Fibrosis Transmembrane Receptor (CFTR). A transmembrane form of the prion protein has been linked to neurodegenerative diseases. (See, Hegde et al., *Science*, 279(5352):827-834, 1998). Several nuclear envelope transmembrane proteins have been associated with signaling functions at the nuclear envelope which is involved in human diseases affecting skeletal muscle development. (See, Chen et al., *BMC Cell Biology*, 7:38, 2006).

The pharmaceutical industry has particularly benefited from the study of such membrane structures. It is estimated that about half of all potential pharmaceutical targets are membrane proteins such as ion channels and G-protein coupled receptors (GPCRs). The pharmaceutical and biotechnology industry have been able to produce and isolate sufficient quantities of a small number of membrane proteins and components to enable characterization of these targets, allowing production of biologics and pharmaceuticals useful in the treatment and prevention of diseases linked to these targets. Furthermore, use of such lipid and lipid-like chemistries has allowed the advancement of such fields as chemotherapy and virology. For instance, modern vaccines have greatly benefited from the development of modern and industrially useful lipid preparations which are highly efficient in triggering precise immunological responses in animals and humans. (See, for instance, Copland et al., "Lipid based particulate formulations for the delivery of antigen," 1 mm. Cell Biol., 83:97-105, 2005). The field of chemotherapy has highly benefited from progressive research performed on specific pharmaceutical emulsions which allow precise targeting and localization of otherwise very poisonous and toxic substances to only cancerous tissues and organs, preventing damage to other healthy tissue. (See, Kishor M. Wasan, "Role of Lipid Excipients in Modifying Oral and Parenteral Drug Delivery: Basic Principles and Biological Examples," John Wiley & Sons, Inc., Hoboken, N.J., 2007; and Davis et al., "Lipid Emulsions as Drug Delivery Systems," *Annals of the New York Acad. Of Sciences*, 507:75-88, December 1987).

A wide variety of lipid and lipid-like molecules, also called surfactants, are disclosed in the literature of various polarities, sizes, hydrophobicities, and the like. Lipid science has advanced to provide a myriad number of variations on sugar-like lipids, phospholipids with polar head groups, lipids with multiple polar head groups, polar head groups varying in polarity, and carbohydrate chains varying in size, composition and properties. Presently provided is a class of carbohydrate surfactants having additional chemical functionality.

The lipid derivatives of the carbohydrates provided here, such as, but not limited to, maltoside-based alkyne and azide derivatives, as well as phosphocholine derivatives. The chemical functionalities imparted to these derivatives may be useful in conjugating them to other groups. The conjugated surfactants may then provide interesting new molecules having unique biochemical and biophysical properties which heretofore have not been available or easily accessible to the modern chemist or biochemist. These novel properties and characteristics provide industry and academia with an expanded arsenal of as yet untested biochemical surfactants, potentially possessing a wide variety of biochemical and biophysical characteristics, which when applied to the study of lipid-bound, or membrane-associated proteins and/or other biochemical components, may yield unprecedented results. This expanded repertoire of combination surfactants may therefore lead to new treatments and perhaps prevention of diseases that have as yet remained intractable due to the nature of the membrane- or lipid-related target to which the disease may be linked.

Among other aspects, the present invention provides compositions of surfactant derivatives and the like, methods of making the same, and methods of using the same, for instance in the formation of micelles and micelle-like structures, that address the above noted needs. A complete understanding of the invention will be obtained upon review of the following.

SUMMARY OF THE INVENTION

Provided are chemical compounds and compositions thereof comprising an azide derivative of a saccharide covalently linked to a variable length carbon chain. The derivative of a saccharide may be a monosaccharide, disaccharide, polysaccharide or oligosaccharide. The disaccharide may be, for instance, β-D-maltose. The variable length carbon chain is between 2 and 20 carbon atoms in length. Specific disclosed chemical compounds and compositions thereof include 11-azido-undecyl-β-D-maltoside and 16-azido-hexadecyl-β-D-maltoside and methods of making the same.

Also provided are chemical compounds and compositions comprising an alkyne derivative of a saccharide covalently linked to a variable length carbon chain. The derivative of a saccharide may be a monosaccharide, disaccharide, polysaccharide or oligosaccharide. The disaccharide may be, for instance, β-D-maltose. The variable length carbon chain is between 2 and 20 carbon atoms in length. Specific disclosed chemical compounds and compositions thereof include 9-decynyl-β-D-maltoside, 10-undecynyl-β-D-maltoside and 12-tridecynyl-β-D-maltoside.

Chemical compounds and compositions thereof disclosed herein include alkyne derivatives of phosphocholine covalently linked to a variable length carbon chain. The variable length carbon chain is between 2 and 20 carbon atoms in length. An exemplary compound is 9-decynyl-1-phosphocholine.

Further provided below are chemical compounds and compositions thereof which include an azide or alkyne derivative of phosphocholine covalently linked to a variable length carbon chain, wherein the variable length carbon chain may be between 2 and 20 carbon atoms in length. A specific example of such phosphocholine derivatives includes 11-azido-undecyl-1-phosphocholine.

Additional compositions provided herein include compositions including an azide or alkyne derivative of a saccharide covalently linked to a variable length carbon chain and an alkyne or azide derivative of phosphocholine covalently linked to a second variable length carbon chain and mixtures thereof. Such compositions typically include an azide of either the saccharide or phosphocholine paired with an alkyne of the non-azide compound, providing a reactable pair which may upon reaction form a 1,4-disubstituted [1,2,3]-triazole.

The present disclosure is further directed to compositions and chemical compounds which are 1,4-disubstituted [1,2,3]-triazoles formed by the reaction under appropriate conditions of an azide or alkyne derivative of a saccharide covalently linked to a variable length carbon chain and an alkyne or azide derivative of phosphocholine covalently linked to a second variable length carbon chain. That is, the compositions are derived from the reaction of an azide with an alkyne species, wherein either azide or alkyne may be phosphocholine or a saccharide so long as at least one azide is present and one alkyne is present. The azide and alkyne derivatives may be one or more of 11-azido-undecyl-β-D-maltoside, 16-azido-hexadecyl-β-D-maltoside, 9-decynyl-1-phosphocholine, 10-undecynyl-β-D-maltoside, 12-tridecynyl-β-D-maltoside, 11-azido-undecyl-1-phosphocholine, and/or 9-decynyl-1-phosphocholine. The variable length carbon chains may be between 2 and 20 carbon atoms in length.

The above-disclosed azide and alkyne derivatives of saccharides and phosphocholines may be covalently linked to form 1,4-disubstituted [1,2,3]-triazoles which possess unique properties useful in the field of membrane biology and the study of membrane associated or membrane-bound proteins and other biochemical components. Thus, further provided herein are methods of forming micelles, bicelles and other such lipid bilayer-like structures using the 1,4-disubstituted [1,2,3]-triazoles provided herein.

DEFINITIONS

Figure 1:
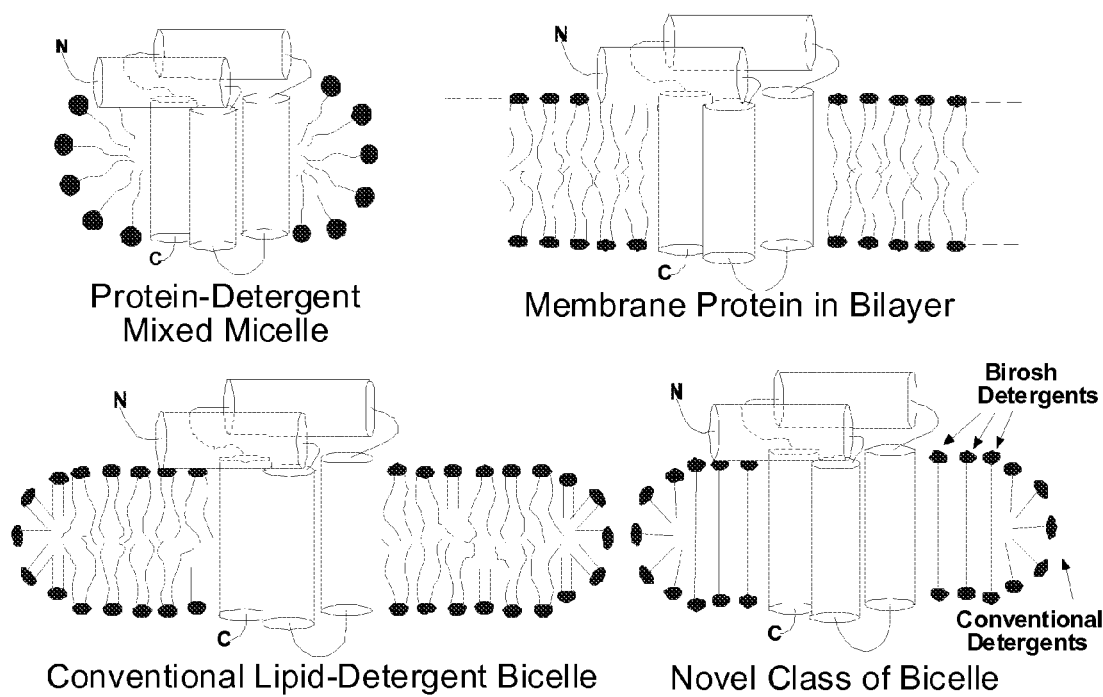
FIG. 1 illustrates various forms of micelle and bicelle structures in the context of a theoretical, exemplary transmembrane protein.
Figure 2:
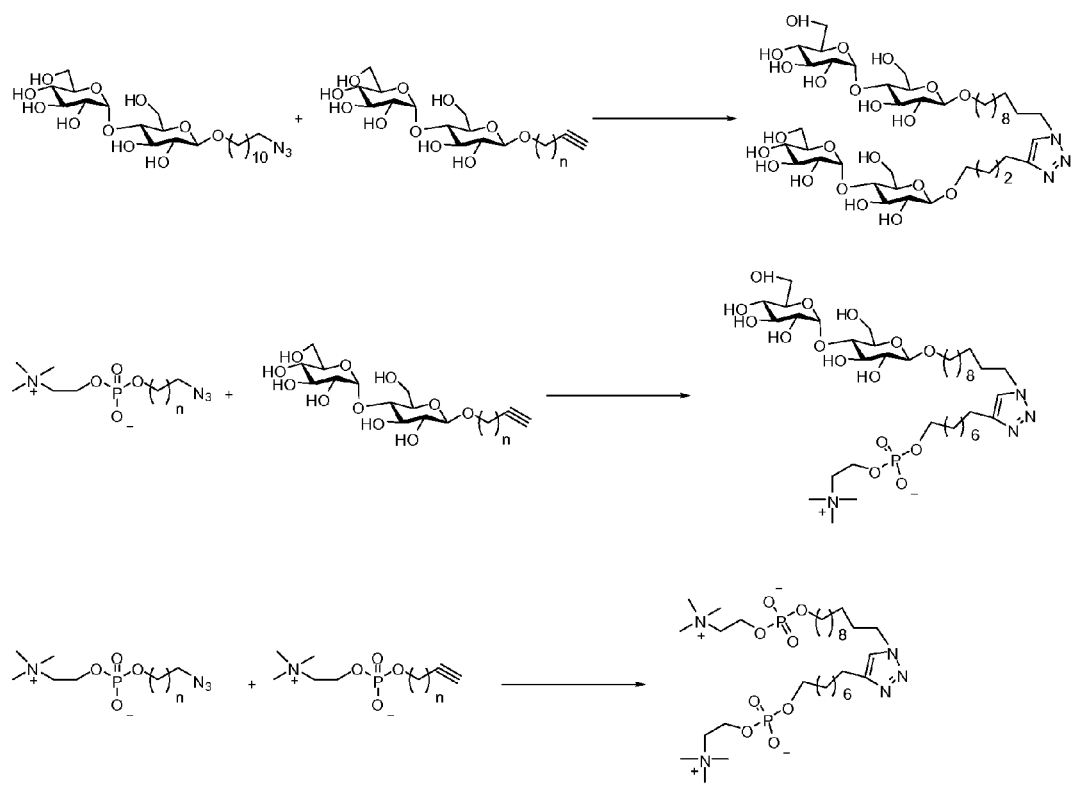
FIG. 2 illustrates various exemplary derivitized maltosides and phosphocholines and resultant 1,4-disubstituted [1,2,3]-triazoles produced upon reaction of the derivitized molecules.
Figure 3:
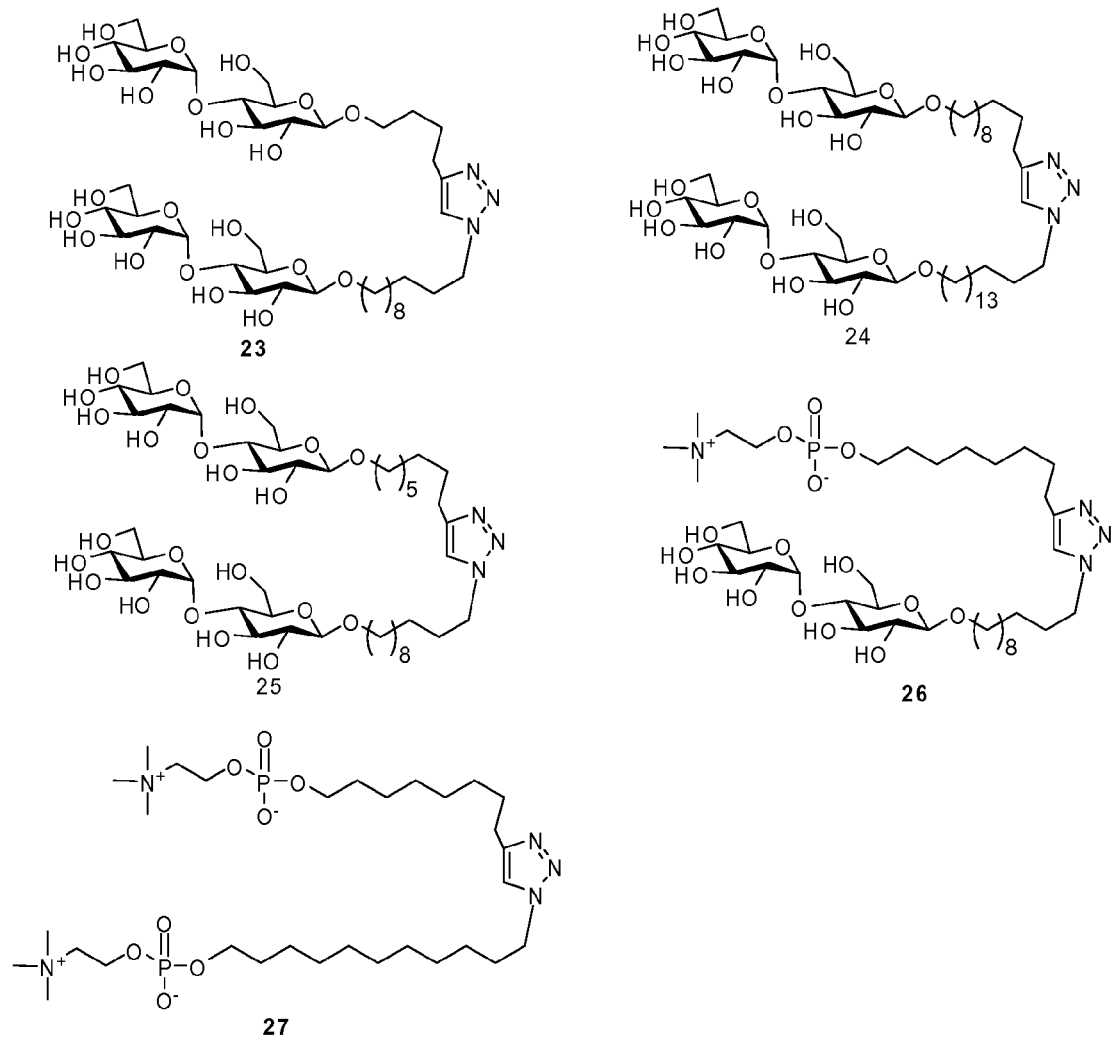
FIG. 3 illustrates various additional exemplary derivitized maltosides and phosphocholines and resultant 1,4-disubstituted [1,2,3]-triazoles produced upon reaction of the derivitized molecules.

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a molecule" includes a plurality of such molecules, and the like.

The term "about" as used herein indicates the value of a given quantity varies by +/−10% of the value, or optionally +/−5% of the value, or in some embodiments, by +/−1% of the value so described.

The term "aliphatic acid" as used herein means any acid attached to an organic compound defined by carbon atoms which form branched or straight, open carbon chains. Aliphatic acid is meant to also include all degrees of acid, such as dicarboxylic acids and tricarboxylic acids.

The term "fatty acid" as used herein refers to $C_4$-$C_{30}$ fatty acids which may be saturated or unsaturated, and may have straight or branched alkyl chains. Fatty acids are defined by a carboxylic head group attached to a carbon chain of $C_4$-$C_{30}$ in length. Examples fatty include, but are not limited to, pentanoic acid, hexanoic acid, heptanoic acid (enanthic acid), octanoic acid (caprylic acid), nonanoic acid (pelargonic acid), decanoic acid (n-capric acid), undecanoic acid, lauric acid, myristic acid, palmitic acid, stearic acid, oleic acid, linolenic acid, linoleic acid, erucic acid, palmitoleic acid, pentadecanoic acid, margaric acid, arachidic acid, arachidonic acid, behenic acid, and soya fatty acids, 2-hexyldecanoic acid, and mixtures thereof and the like.

As known in the art, an unsaturated fatty acid ester is the ester condensation product of an unsaturated fatty acid and an alcohol. The unsaturated fatty acid comprises an extended carbon chain containing at least one carbon-carbon double bond and terminating in a carboxylic acid group. Typically, the unsaturated fatty acid will contain greater than about 6 carbon atoms, greater than about 10 carbon atoms, or greater than about 12 carbon atoms. Typically, the unsaturated fatty acid will contain less than about 50 carbon atoms, less than about 36 carbon atoms, or less than about 26 carbon atoms. At least one carbon-carbon double bond is present along the carbon chain in an unsaturated fatty acid. This double bond usually occurs at about the middle of the chain, but not necessarily at this position. The unsaturated fatty acid may be straight chain or branched and substituted along the fatty acid chain with one or more substituents. Non-limiting examples of substituents include alkyl moieties, including for example methyl, ethyl, propyl, butyl, and the like; cycloalkyl moieties, including for example, cyclopentyl and cyclohexyl; monocyclic aromatic moieties, such as, but not limited to, phenyl; arylalkyl moieties, arylalkyl moieties, including, for example, benzyl; and alkylaryl moieties, including, for example, tolyl, ethylphenyl, xylyl, and the like; as well as hydroxyl, ether, keto, aldehyde, and halide, such as chloro and bromo, functionalities.

Non-limiting examples of unsaturated fatty acids that may be acted upon by the present compositions and methods include 3-hexenoic (hydrosorbic), trans-2-heptenoic, 2-octenoic, 2-nonenoic, cis- and trans-4-decenoic, 9-decenoic (caproleic), 10-undecenoic (undecylenic), trans-3-dodecenoic (linderic), tridecenoic, cis-9-tetradeceonic (myristoleic), pentadecenoic, cis-9-hexadecenoic (cis-9-palmitoelic), trans-9-hexadecenoic (trans-9-palmitoleic), 9-heptadecenoic, cis-6-octadecenoic (petroselinic), trans-6-octadecenoic (petroselaidic), cis-9-octadecenoic (oleic), trans-9-octadecenoic (elaidic), cis-11-octadecenoic, trans-11-octadecenoic (vaccenic), cis-5-eicosenoic, cis-9-eicosenoic (godoleic), cis-11-docosenoic (cetoleic), cis-13-docosenoic (erucic), trans-13-docosenoic (brassidic), cis-15-tetracosenoic (selacholeic), cis-17-hexacosenoic (ximenic), and cis-21-triacontenoic (lumequeic) acids, as well as 2,4-hexadienoic (sorbic), cis-9-cis-12-octadecadienoic (linoleic), cis-9-cis-12-cis-15-octadecatrienoic (linolenic), eleostearic, 12-hydroxy-cis-9-octadecenoic (ricinoleic), cis-5-docosenoic, cis-5,13-docosadienoic and like acids and mixtures thereof.

A non-limiting list of exemplary saturated fatty acids without additional substituents includes the following (common names provided in parentheses): propanoic acid (propionic acid), butanoic acid (butyric acid), pentanoic acid (valeric acid), hexanoic acid (caproic acid), heptanoic acid (enanthic acid), octanoic acid (caprylic acid), nonanoic acid (pelargonic acid), decanoic acid (capric acid), undecanoic acid (undecylic acid), dodecanoic acid (lauric acid), tridecanoic acid (tridecylic acid), tetradecanoic acid (myristic acid), pentadecanoic acid (pentadecylic acid), hexadecanoic acid (palmitic acid), heptadecanoic acid (margaric acid), octadecanoic acid (stearic acid), nonadecanoic acid (nonadecylic acid), eicosanoic acid (arachidic acid), heneicosanoic acid (heneicosylic acid), docosanoic acid (behenic acid), tricosanoic acid (tricosylic acid), tetracosanoic acid (lignoceric acid), pentacosanoic acid (pentacosylic acid), hexacosanoic acid (cerotic acid), heptacosanoic acid (heptacosylic acid), octacosanoic acid (montanic acid), nonacosanoic acid (nonacosylic acid), triacontanoic acid (melissic acid), henatriacontanoic acid (henatriacontylic acid), dotriacontanoic acid (lacceroic acid), tritriacontanoic acid (psyllic acid), teratriacontanoic acid (geddic acid), pentatriacontanoic acid (ceroplastic acid), hexatriacontanoic acid (hexatriacontylic acid) and mixtures thereof.

The term "carbohydrate" is meant to mean a compound, substituted or unsubstituted, having the general formula $C_m(H_2O)_n$, which is primarily composed of carbon, hydrogen and oxygen in the atom ratio of 1:2:1. Carbohydrates are most commonly found as polyhydroxy aldehydes or ketones and are also commonly referred to in biochemistry as saccharides or sugars. Saccharides may exist is mono-saccharides, disaccharides, oligosaccharides and polysaccharides. They may vary in length from single sugar molecules to repeating units of hundreds or thousands of sugar molecules. Commonly known saccharides include, but are not limited to, glyceraldehyde, dihydroxyacetone, erythrose, threose, ribose, deoxyribose, lyxose, arabinose, xylose, allose, altrose, glucose, mannose, gulose, idose, galactose, talose, dihydroxyacetone, erythrulose, ribulose, xylulose, psicose, fructose, sorbose, tagatose, mannoheptulose, sedoheptulose, octolose, 2-keto-3-deoxy-manno-octonate and sialose. Other saccharides exist which are derivatives of these exemplary and commonly known saccharides. Common disaccharides include, but are not limited to, sucrose, lactose, maltose (two glucose molecules), isomaltose, trehalose, gentiobiose, laminaribiose, mannobiose, xylobiose and cellobiose. Higher order saccharides include, for example, amylase, amylopectin, glycogen, cellulose, starch, chitin, heparin, dextran, and the like. Saccharides are known to play many very important roles in biology and biochemistry as structural components, chemical mediators and modulators in many different signaling pathways involving various enzymes and cells.

The term "micelle" is meant to mean an aggregate of surfactant molecules dispersed in a liquid colloid comprised of amphiphilic molecules having a greasy carbon chain tail and a polar head group. The aggregate typically forms a spherical structure wherein the polar head group surrounds the outer surface of the spheroid in an aqueous solution, protecting the hyrdrophobic carbon chain tail from exposure to water in the center of the sphere. Various amphiphilic molecules, such as fatty acids, detergents, surfactants, phospholipids and the like are capable of forming micelles. Micelles can range in size from about a few hundred Angstrom to several nanometers. For instance, micelles may range in size from approximately 200 Angstrom or less to about 20 nm or more. Micelle is meant to include other such aggregates such as bicelles, bilayer fragments and other multilamellar arrangements or lipid bilayers of various geometries capable of forming in the presence of amphiphilic molecules.

A variety of additional terms are defined or otherwise characterized herein.

DETAILED DESCRIPTION

The present invention provides compounds and derivatives thereof, methods of using the compounds and derivatives thereof, and methods of synthesizing compounds and derivatives thereof.

A general class of embodiments includes compounds which are capable, upon derivatization, of forming micelles or micelle-like structures. The compounds in particular include a derivatized saccharide and a derivatized phosphocholine molecule. The derivatized saccharides include, for instance, azide or alkyne derivatized saccharide. The saccharide may be any one of a number of known saccharides or disaccharides, such as, for instance, maltose which may be otherwise substituted or unsubstituted. Additionally, a derivatized phosphocholine molecule may include, for instance, an azide or alkyne derivative thereof. The present compound embodiments include compositions comprised of both derivatized saccharide and derivatized phosphocholine, which may be used together in certain applications and methods.

The derivatized saccharide may be, for instance, either an azide maltoside or an alkyne maltoside. The maltoside may itself have any number of additional chemical functional groups located on the structure as a substituted or unsubstituted maltoside. The maltoside may have a variable-length carbon chain attached to a terminal hydroxyl, forming an ether linkage. The carbon chain may comprise any number of carbons from about 2 to about 20, depending on the desired hydrophobicity of the resulting end product maltoside derivative. The azide may therefore be present at the opposite end of the carbon chain such that the maltose sugar moieties are present at one end of the carbon chain covalently attached via an ether linkage and the azide or alkyne moiety is present at the opposite end of the variable length carbon chain. By varying the length of the carbon chain, the degree of hydrophobicity may be controlled. Furthermore, the carbon chain may be substituted by other hydrophobic or hydrophilic groups, such as, but not limited to, hydroxyls, acids, carbonyls, amides, amines, sulfhydryls, sulfones, alkenes, alkanes, aromatic groups and the like.

The derivatized phosphocholine may be, for instance, either an azide maltoside or an alkyne maltoside. The phosphocholine derivate may be, for instance, covalently attached at one end of a variable length carbon chain. The variable length carbon chain may be any desired length. For instance, the chain length may be anywhere from about 2 atoms to, for instance, 20 atoms in length. At the opposite end of the variable length carbon chain there may be covalently attached an azide or alkyne moiety. The length of the variable length carbon chain may be adjusted such that the end molecule exhibits the desired hydrophobic properties.

The derivatized saccharide may therefore be reacted with either another derivatized saccharide, or alternatively with a derivatized phosphocholine molecule. The reaction of azides with alkynes under conditions which promote cycloaddition to form a 1,4-disubstituted 1,2,3-triazole structure. (See, for instance, U.S. Pat. Nos. 7,763,736, 7,709,655, 7,375,234 and 7,618,944, all of which are incorporated herein by reference in their entireties for all purposes). The chemistry reactions employed are commonly referred to as "click chemistry," though these molecules may be employed in many other useful manners, such as in Staudinger chemical reactions and the like. (See, for example, Jewett et al., *J. Am. Chem. Soc.*, 132(11):3688-3690, 2010). Furthermore, many known reactions exist for azides and alkynes. Thus, these derivatized molecules may serve as highly useful intermediates which may be further reacted to form additional useful and custom-tailored molecules for other applications. The resultant molecules, combining the derivatized saccharide with the derivatized phosphocholine, offers unusually exceptional flexibility in custom-tailoring large molecules of variable carbon chain length. Such large molecules may be designed such that they possess the precise degree of hydrophobicity for the intended purpose or use of the molecules.

Upon formation of the saccharide-saccharide molecules, or saccharide-phosphocholine molecules, sufficient quantities may be easily obtained to form micelles or micelle-like structures which may then be used in experiments designed to isolate and/or characterize membrane proteins or membrane associated biochemical components. Additional applications include, but are not limited to, for instance, attachment of various saccharides to a solid support for the purpose of forming a substrate-bound micelle or lipid bilayer and the like. Alternatively such chemistries may be used to attach the saccharides to a solid support for the purpose of binding other membrane associated proteins and biochemical components also to the solid support as a means of purification of the desired target. Optional washing and eluting steps may also be implemented as desired.

The solid support may be, for instance, comprised of glass, silica, plastic, metal or any other known combination of such materials useful for the study of biochemical complexes. For instances, many such substrates are employed in microarrays used in nucleic acid analyses and surface plasmon resonance (SPR) applications for the study of proteins and other small biochemical components.

In other embodiments, the derivatized saccharides may be reacted with proteins, enzymes and/or other cellular components to modify the biochemical properties of the target. The addition of such functional groups to proteins or other cellular components may be an efficient means of tagging, modulation activity, altering inter-cellular targeting, stabilizing, and/or studying the characteristics of the modified target either in vitro or in vivo (if appropriate fluorescent/chemiluminescent/radioactive, and the like, labels are employed according to known means).

Other embodiments employing the derivatized chemicals disclosed herein involve the formation of a bicelle in situ, which will incorporate and thereby enhance the thermal stability or otherwise alter the biophysical and/or biochemical properties of the intended membrane-associated target. There are several different means of accomplishing this goal. For instance, a known standard extraction/purification protocol may be employed for the desired target, after which a 1:1 mixture of the azide/alkyne derivatized saccharide components may be added. The derivatized components may then be reacted by addition of, for instance, copper sulfate and sodium ascorbate to provide the bicelle mimic. Alternatively, the target may be purified using one derivatized saccharide, followed by addition of the second derivatized component and reaction with copper sulfate and sodium ascorbate to form the bicelle.

In all instances, the variable length carbon chain covalently linked to either the derivatized saccharide or the derivatized phosphocholine may be covalently linked at any convenient location on the saccharide or phosphocholine molecule accessible by known modern organic chemistry techniques (as exemplified below, for instance). The variable length carbon chains may in general be anywhere from 2 to 20 carbon atoms in length. For instance, the carbon chain may be 2, 3, 4, 5, 6, 7, 8, 9, 10, 11, 12, 13, 14, 15, 16, 17, 18, 19 or even 20 carbon atoms in length. The length of the variable carbon chain may be varied depending on the desired properties of the resultant 1,4-disubstituted [1,2,3]-triazole useful in the downstream applications of such molecules described herein. Furthermore, the covalently linked carbon chain may be optional either to the saccharide derivative or the phosphocholine derivative. In other words, upon formation of the final 1,4-disubstituted[1,2,3]-triazole from either two derivatized saccharides or a derivatized saccharide and a derivatized phosphocholine, either one or both derivatized starting materials may have such a variable length carbon chain attached thereto.

Furthermore, compositions comprising the resultant 1,4-disubstituted [1,2,3]-triazole compounds may be a mixture of varying lengths of the variable length carbon chain. That is, the composition may comprise, for instance, a 1:2:3 ratio of 1,4-disubstituted [1,2,3]-triazoles derived from 1) a derivatized saccharide having a 12 carbon length carbon chain and a derivatized phosphocholine having a 5-carbon length carbon chain, 2) a derivatized saccharide having a 9 carbon length carbon chain and a derivatized phosphocholine having a 9 carbon length carbon chain, and 3) a derivatized saccharide having a 10 carbon length carbon chain and a derivatized phosphocholine having a 3 carbon length carbon chain, for example. Other similar combinations and mixtures may be developed as needed for the intended method of lipid study or downstream application.

The identity of the resultant 1,4-disubstituted [1,2,3]-triazole formed from the reaction of the derivatized saccharide and phosphocholine may be any number of such combinations using any one or more of the saccharides identified herein. For instance, some non-limiting exemplary starting derivatized reactants may be one or more of 11-azido-undecyl-β-D-maltoside, 16-azido-hexadecyl-β-D-maltoside, 9-decynyl-1-phosphocholine, 10-undecynyl-β-D-maltoside, 12-tridecynyl-β-D-maltoside, 11-azido-undecyl-1-phosphocholine, and/or 9-decynyl-1-phosphocholine. While these are merely exemplary derivatized azide and alkyne saccharides and phosphocholines, one of skill in the art will know that any saccharide amenable to the reaction chemistry provided herein can be substituted for these exemplary molecules. Furthermore, longer or shorter carbon chains may be employed as indicated above to create even further additional possible amphiphilic molecules. That is to say, the presently disclosed methods and compounds offer a large array of possible combinations and compounds which when used to form the resultant 1,4-disubstituted [1,2,3]-triazoles can provide highly advantageous and unusual amphiphilic properties useful in the study of membrane associated and membrane bound proteins and other biochemical components. One of skill in the art, in the light of the present disclosure, will understand the scope and possibilities provided herein for providing large libraries of such 1,4-disubstituted [1,2,3]-triazole compounds for such studies.

Therefore, also disclosed herein are kits and complex compositions comprising 2-10 or more different 1,4-disubstituted [1,2,3]-triazole compounds created by reaction of saccharide alkyne or azide derivatives and/or phosphocholine alkyne or azide derivatives to create a wide variety of amphiphilic molecules designed for such membrane protein studies. Kits may even comprise 10-15 different 1,4-disubstituted [1,2,3]-triazole compounds created by these methods, or 15-20 different compounds, or 20-25 different compounds, or 25-50 different compounds, or as many as 50-75 different compounds.

Such kits and compositions as disclosed herein may have the different compounds already pre-immobilized on a substrate for specific types of membrane protein studies. The 1,4-disubstituted [1,2,3]-triazole compounds created by these methods may be located in different addressable locations on the substrate such that binding to one addressable feature may indicate to the user which 1,4-disubstituted [1,2,3]-triazole best binds to the target membrane protein or membrane component. That is, each addressable feature on the substrate may contain a known 1,4-disubstituted [1,2,3]-triazole made using the present methods and compositions. Incubation of such a substrate with the target sample, i.e. a sample comprising the target membrane protein or membrane component, such that binding occurs, will enable detection of which 1,4-disubstituted [1,2,3]-triazole best interacts with the target membrane molecule or component. Various labeling techniques may be employed such as, for instance, chemiluminescence, fluorescence, radioactivity, phosphorescence, plasmon resonance and the like.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1

Saccharide derivatives were synthesized. As exemplary compounds for this example, maltosides were selected as the saccharide. Substituted maltosides could have also been used in an equivalent manner. Furthermore, other mono- and disaccharides could also be employed in a like manner to arrive at the corresponding alkyne and azide derivatives shown here.
diisobutyl aluminum hydride
Reduction of Methyl Ester to Alcohol:
To a cooled solution (−60° C.) of methyl ester (10 g, 1 or 3) in dry dichloromethane (DCM, 300 mL) was added DIBAL-H (diisobutyl aluminum hydride, 2.5 eq., 2M solution in hexanes) in a dropwise manner. The resulting reaction mixture was allowed to warm to 0° C. over 4-5 hrs. (See, Scheme I, below). A saturated aqueous solution of sodium potassium tetratatrate (300 mL) was then added to the reaction mixture and was kept stirring overnight. The organic phase was separated, dried over anhydrous sodium sulfate ($Na_2SO_4$) and concentrated under reduced pressure to obtain 4 (oil, 84%) and 2 (white solid, 85%) from 3 and 1 respectively. The crude products were then directly used in the next step without further purification (respective structures were confirmed by $^1$H-NMR).

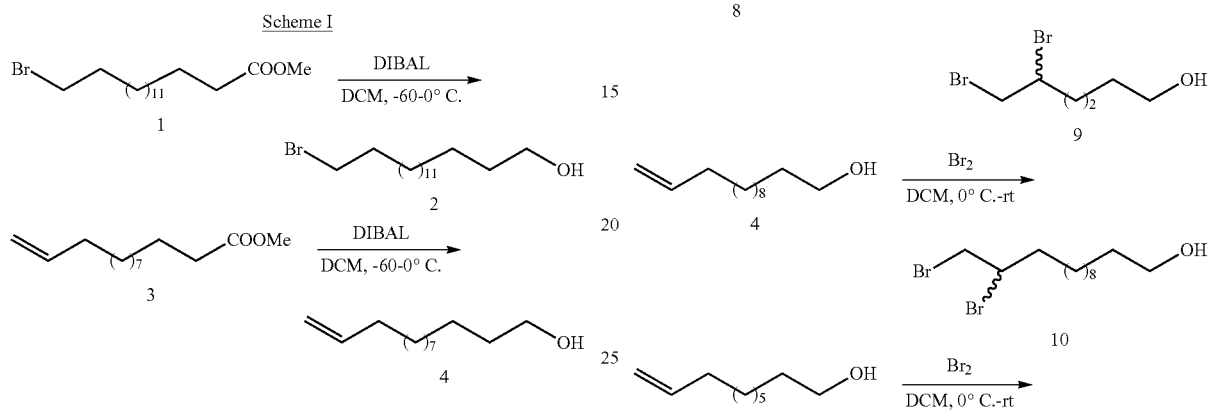

Replacement of Bromide with Azide:

To a solution of 1-hydroxy alkyl bromide compound (10 g, 2 or 6) in dry dimethylformamide (DMF, 200 mL) was added sodium azide (1.5 eq.) at room temperature. (See, Scheme II, below). The solution was then stirred for 48 hrs and monitored by thin layer chromatography (TLC) to confirm disappearance of starting material. The reaction mixture was then added slowly to ice-water (1 L) and was extracted with ethyl acetate (EtOAc, 1 L×3 times). The organic layer were combined, dried over anhydrous sodium sulfate ($Na_2SO_4$) and concentrated under reduced pressure to obtain the crude product 5 (90%) and 7 (89%) from 2 and 6 respectively. The crude products were then directly used in the next step without further purification (respective structures were confirmed by $^1$H-NMR).

Bromination of Alkene:

To a cooled solution (0° C.) of 1-hydroxy alkene (9 g, 4 or 8 or 11) in dry DCM (300 mL) was added bromine (1.05 eq.) in a dropwise manner. (See, Scheme III, below). The resulting reaction mixture was then allowed to attain room temperature overnight. The reaction mixture was extracted with water (300 mL, 3 times). The organic phase was separated, dried over anhydrous sodium sulfate ($Na_2SO_4$) and concentrated under reduced pressure to obtain the crude dibromo alcohols 10 (orange oil, 84%), 9 (orange oil, 88%), and 12 (orange oil, 95%) from 4, 8 and 11 respectively. The crude products were then directly used in the next step without further purification.

Debromination:

To a stirring solution of dibromo-alcohol (8 g, 9 or 10 or 12) in t-butanol (250 mL) was added t-butoxide (t-BuOK, 2.5 e.q.) at 40° C., and the resulting solution was then refluxed for 24 hrs until most of starting material was converted as confirmed by thin-layer chromatography (TLC, in Hexane:DCM:EtOAc, 5:1:1). (See, Scheme IV, below). The solution was then cooled down to room temperature and extracted with EtOAc and water. The organic phase was separated, dried over sodium sulfate and concentrated under reduced pressure to obtain a mixture (in a ratio of about 5:1) of alkynyl alcohol 13-15 and partially-debrominated product 13'-15' from 9, 10 and 12 respectively. The crude products were then directly used in the next step without further purification.

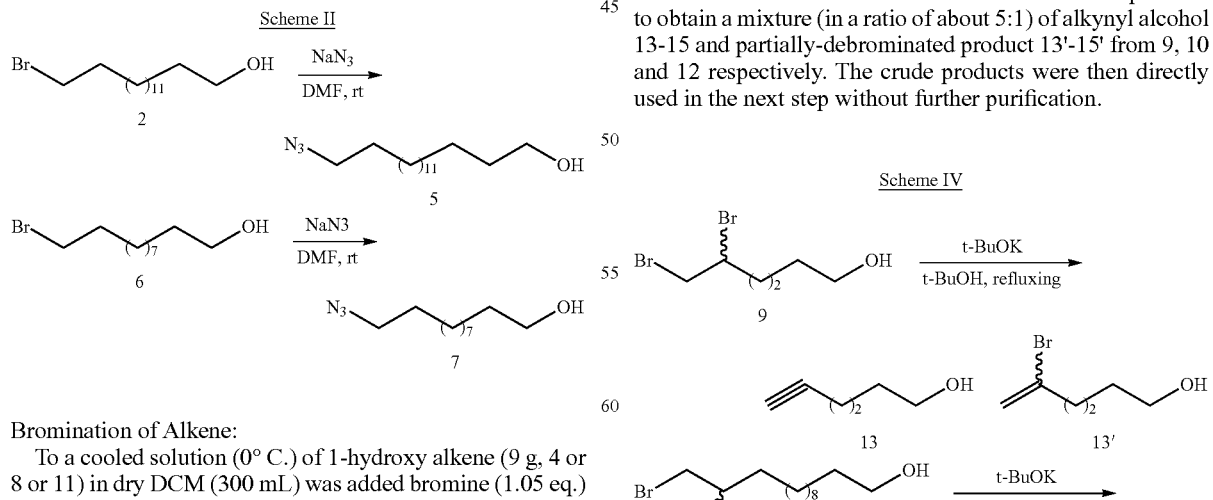

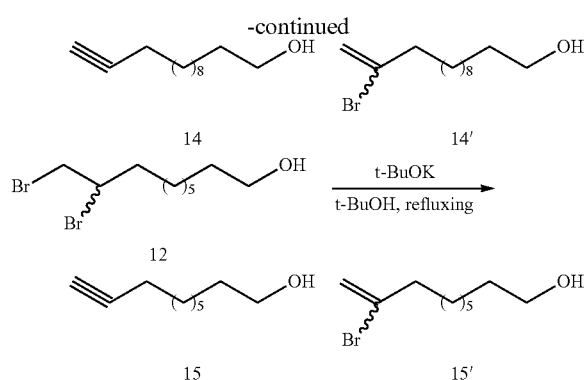

Glycoyslation and Deprotection:

To a cooled (−15° C.) stirring solution of bromo perbenzoylated maltose (BBM) and azido- or alkynyl-derivatized alcohol, in 300 mL of solvent (DCM and MeCN, ratio 5:1) with activated molecular sieves was added silver trifluoromethane sulfonate (AgOTf, 1.2 e.q.). (See, Scheme V, below). The resulting mixture was allowed to attain room temperature overnight. After completion of reaction (ca. 24 hrs), the reaction mixture was quenched with triethylamine (1.2 eq) and filtered to afford the crude product, which was then subjected to a normal phase chromatography via silica gel to obtain the desired product. Following the standard deprotection protocol (Zemplén de-O-acetylation), final product was obtained after purification by C-18 reverse phase column chromatography.

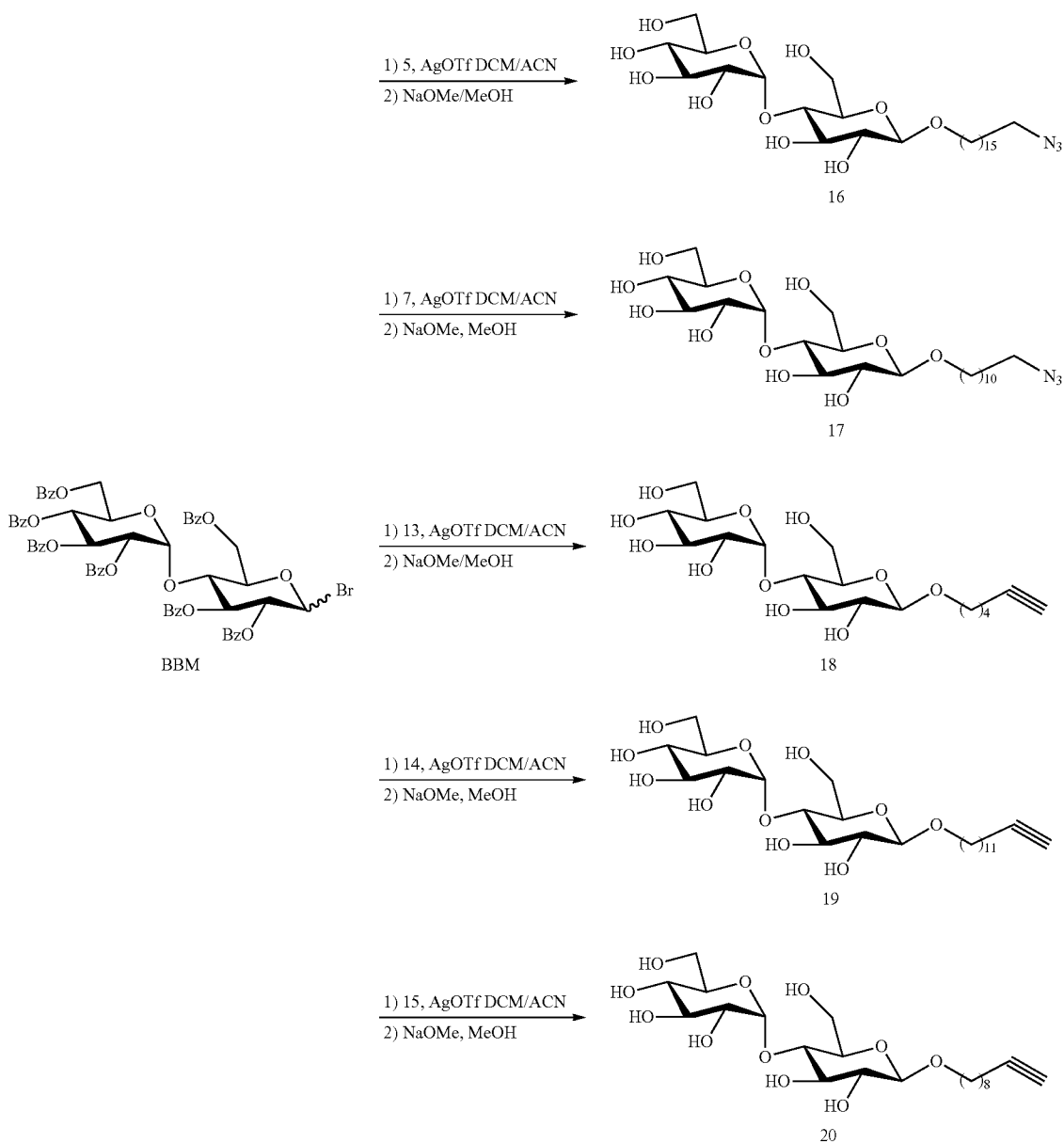

Example 2

Azide and alkyne derivatives of phosphocholine molecules having a variable length carbon chain were prepared as follows. Following the standard procedure, two phosphocolines, 21 and 22, with azide or alkyne functional groups were synthesized. (See, Scheme VI, below).

Scheme VI

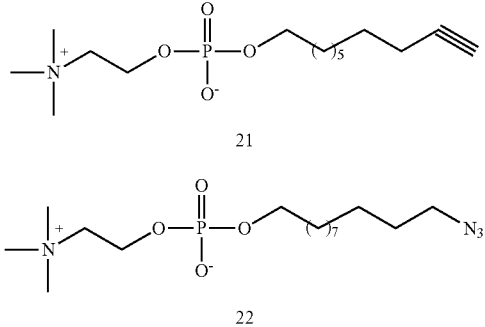

Generally, this procedure was accomplished as follows. To a 5 L, 3-necked round bottom flask provided with an overhead stirrer, temperature probe, pressure equalized dropping funnel with drying tube and a dry ice/methanol bath, was added 112 ml $POCl_3$ and 100 ml THF which was stirred for 10 minutes. In a 2-L Erlenmeyer, 1000 ml THF, 1 mole starting alcohol, and 153 ml triethylamine were mixed. The solution was transferred to the dropping funnel and the addition begun. Once the addition is complete, the flask is stirred for 30 minutes. The flask may also be warmed by stirring overnight. This yields the intermediate alkyl dichlorophosphate.

Next, to a 2 L Erlenmeyer was added 1500 ml THF, 73 ml ethanolamine, and 335 ml triethylamine which was stirred. This solution was transferred to the dropping funnel to begin the addition, which was conducted at <0° C. for about 1 hr. The reaction was stirred for an additional 60 minutes to 24 hrs. The reaction mixture was filtered using a 2 L coarse fritted funnel and filter flask to remove precipitated triethylamine-HCl (TEA-HCl). The precipitate was rinsed with about 1 L of THF. The filtrate was aspirated at about 60° C. until it forms a thick syrup using a cold trap when aspirating to reduce the amount of THF fumes produced. The resultant alkyl-2-oxo-1,2,3-oxazaphospholane intermediate presented as a syrup which was cooled for 10-15 minutes.

To prepare the next intermediate, alkylphosphoethanolamine, to a 500 ml Erlenmeyer, 235 ml glacial acetic acid and 100 ml DI water were added and mixed. This acid solution was carefully added to the alkyl-2-oxo-1,2,3-oxazaphospholane intermediate syrup from above. Using a 5 L, 3-necked round bottom flask equipped with a temperature probe, overhead stirrer, and a dropping funnel in a methanol/dry ice bath, the acid solution was added to the pot. The temperature was maintained at <35° C. and stirred for an additional 45 minutes. The product was precipitated using about 2-3 liters of acetone under refrigeration. The solution was filtered using a large Buchner funnel and filter flask and then transferred to a Pyrex dish and dried under vacuum for 1-2 days.

The resultant alkylphosphoethanolamine was immediately used to form the next intermediate of alkylphosphocholine using the following procedure. To a 5 L, 3-necked flask equipped with a dropping funnel, temperature probe, heating mantle and overhead stirrer was added 1080 ml isopropanol, 360 ml dichloromethane, and 0.9 mole of the alkylphosphoethanolamine intermediate. The mixture was heated to about 40° C. Potassium carbonate (126 grams) was dissolved in 180 ml DI water and added to the pot. Dimethyl sulfate (77 ml) was dissolved in 45 ml isopropanol and transferred to the dropping funnel. The rate of addition of these reagents was adjusted to require about 1 hour. The reaction was stirred for 30 minutes once the addition was complete. Dimethyl sulfate (50 ml) was dissolved in 45 ml isopropanol and added dropwise to the reaction (this took about 30 minute to complete this addition). Potassium carbonate (74 grams) was dissolved in 90 ml DI water and added dropwise to the reaction (taking about another 45 minute for this addition). The reaction was then stirred overnight at room temperature. The solution was then filtered and transferred into a 4 L seperatory funnel. About 250 ml isopropanol was used to wash the solid. The top layer was aspirated to a thick syrup of about 650 ml volume. Then the syrup was dissolved using approximately 2 L methanol and refrigerated overnight. The precipitate was filtered and aspirated or rotovapped to a syrup. The syrup was then dissolved in about 1500 ml of DI water and 250 grams of Rexyn was added to the solution and stirred to achieve the desired conductance.

Example 3

Alkyne and azide derivatives were combined to form new molecules having novel properties. In the present example, the maltoside and phosphocoline derivatives prepared in Examples 1 and 2, above, were reacted together to form the resultant 1,4-disubstituted [1,2,3]-triazole compounds. To a round bottom flask with the above substrate pair in 10% solution in water (some MeOH is added if the solution is cloudy) were added $CuSO_4$ (0.1 e.q.) and sodium ascobate (0.2 e.q.). The reaction mixture was stirred overnight and purified by a C-18 column the next day with methanol and water as mobile phase to afford the desire products. (See, Scheme VII, below).

Scheme VII

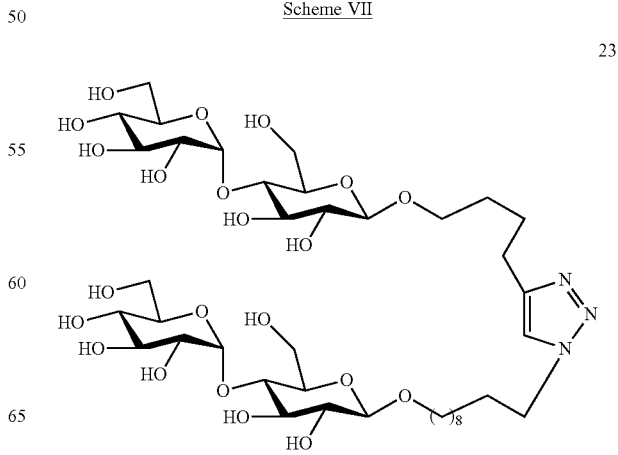

-continued

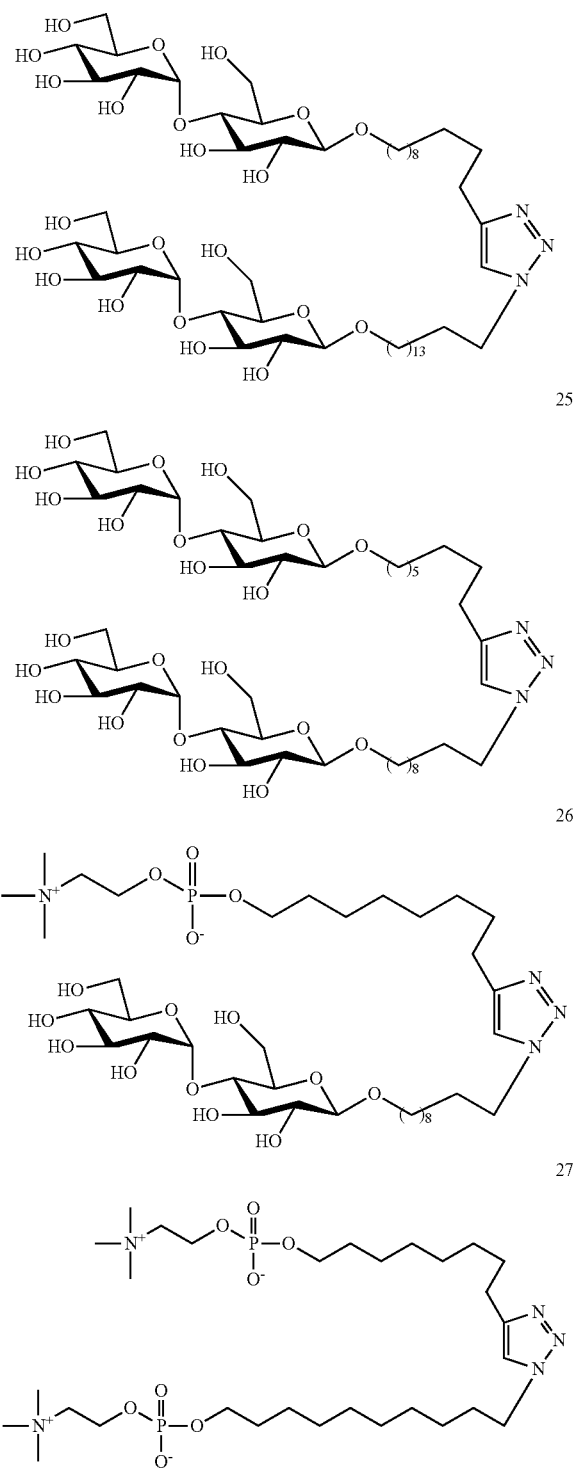

The corresponding critical micelle concentration (CMC) concentration by following standard procedures. The results revealed that the CMC of compound 25 was about 1.42 M. Based on these preliminary results, it appeared that the molecules with phosphocoline units possess a higher water solubility than their corresponding maltosides.

Figure 4A:
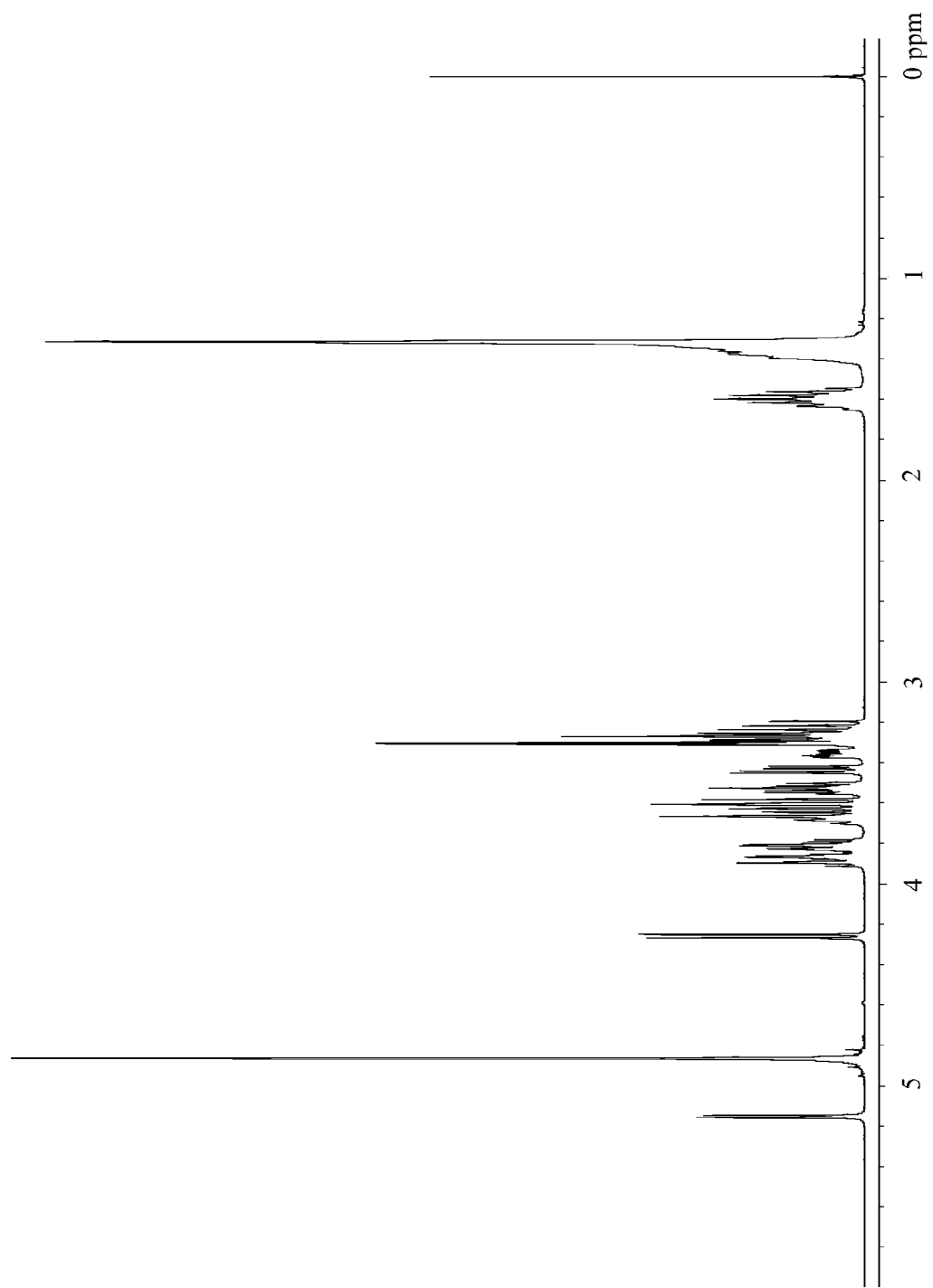
FIG. 4A-FIG. 4C are data obtained from $^1$H NMR, HPLC and MS analysis, respectively, of exemplary maltose azide derivative compound 11-azido-undecyl-β-maltoside.
Figure 4B:
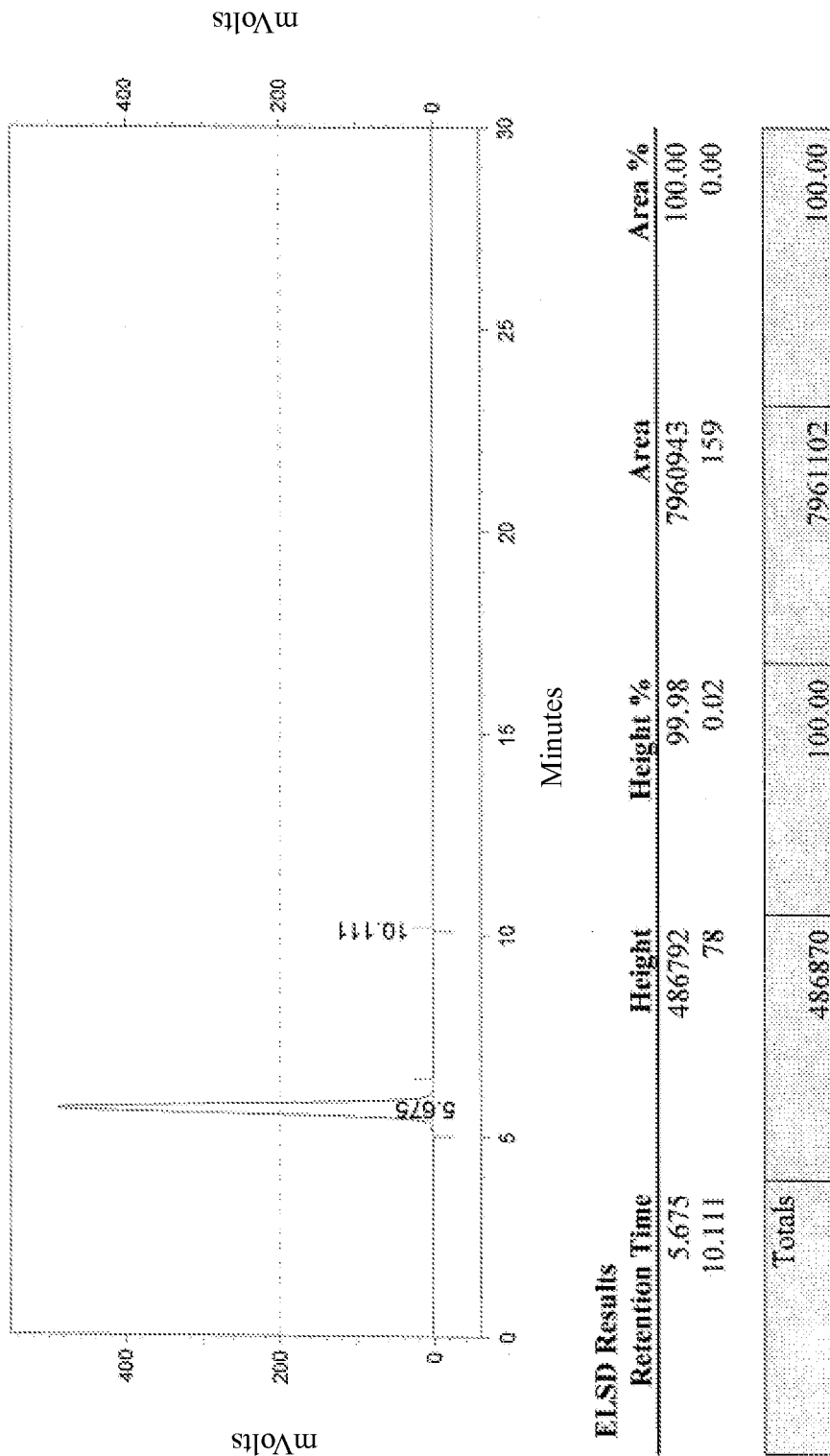
Figure 4C:
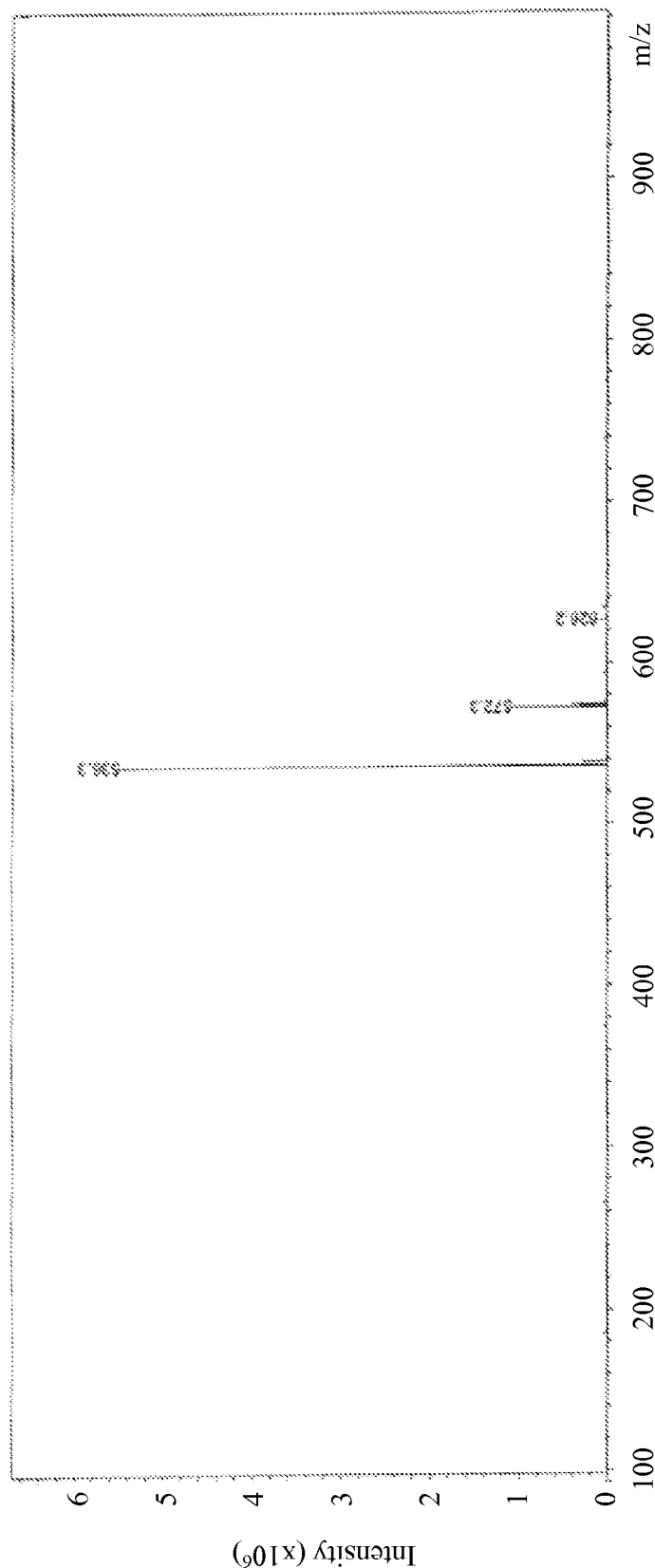
Figure 5A:
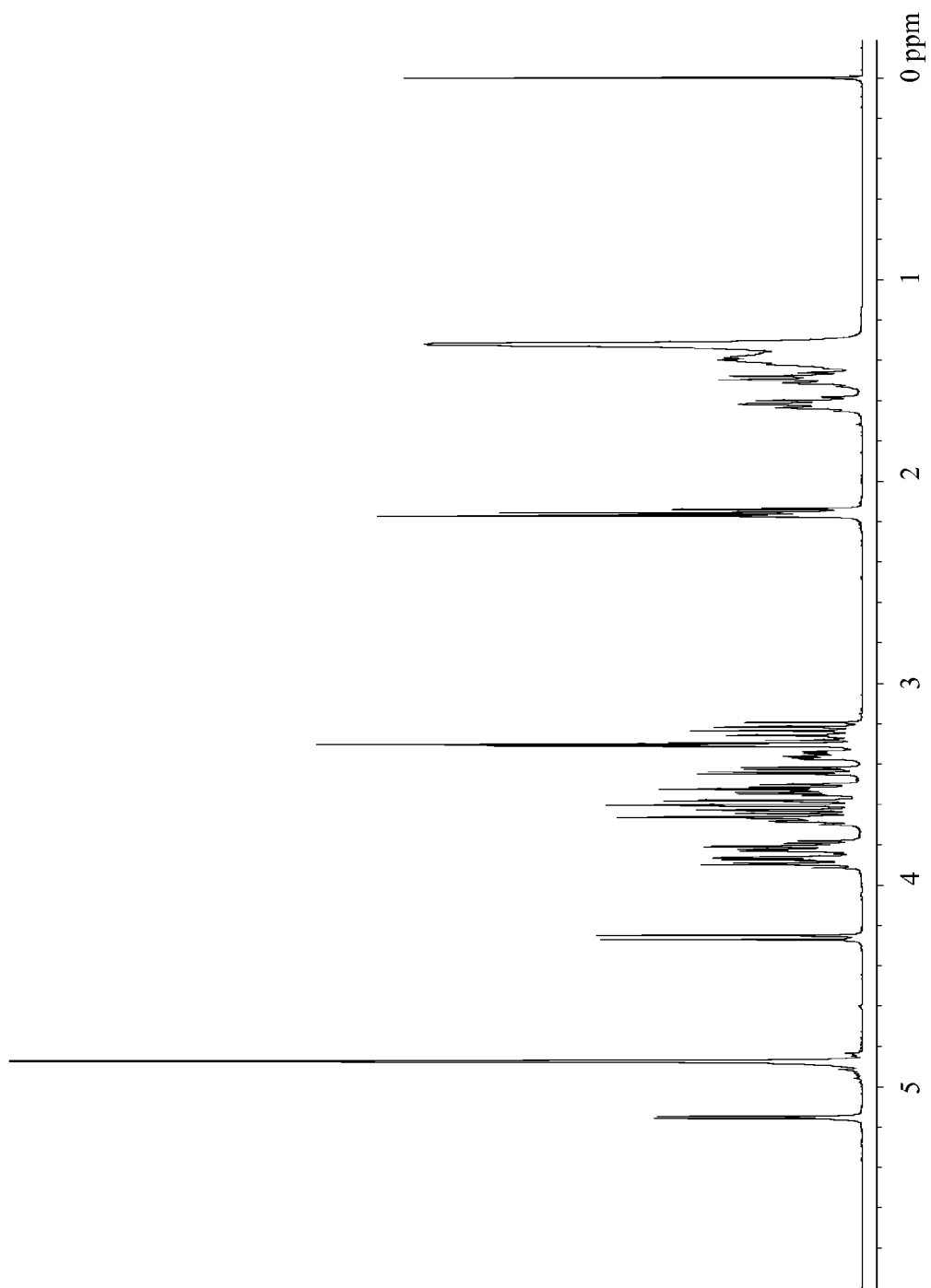
FIG. 5A-FIG. 5C are data obtained from $^1$H NMR, HPLC and MS analysis, respectively, of exemplary maltose alkyne derivative compound 10-undecynyl-β-D-maltoside.
Figure 5B:
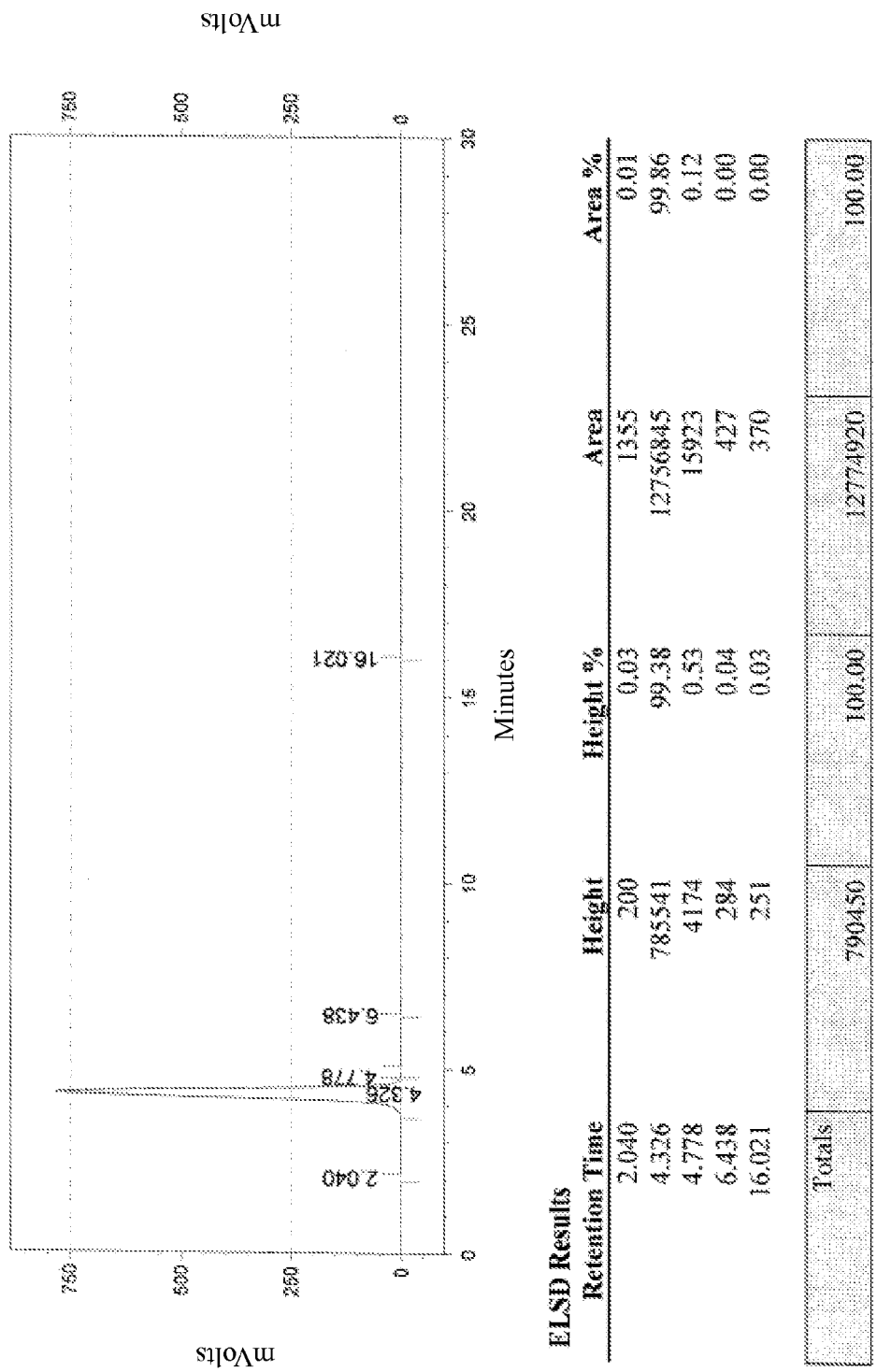
Figure 5C:
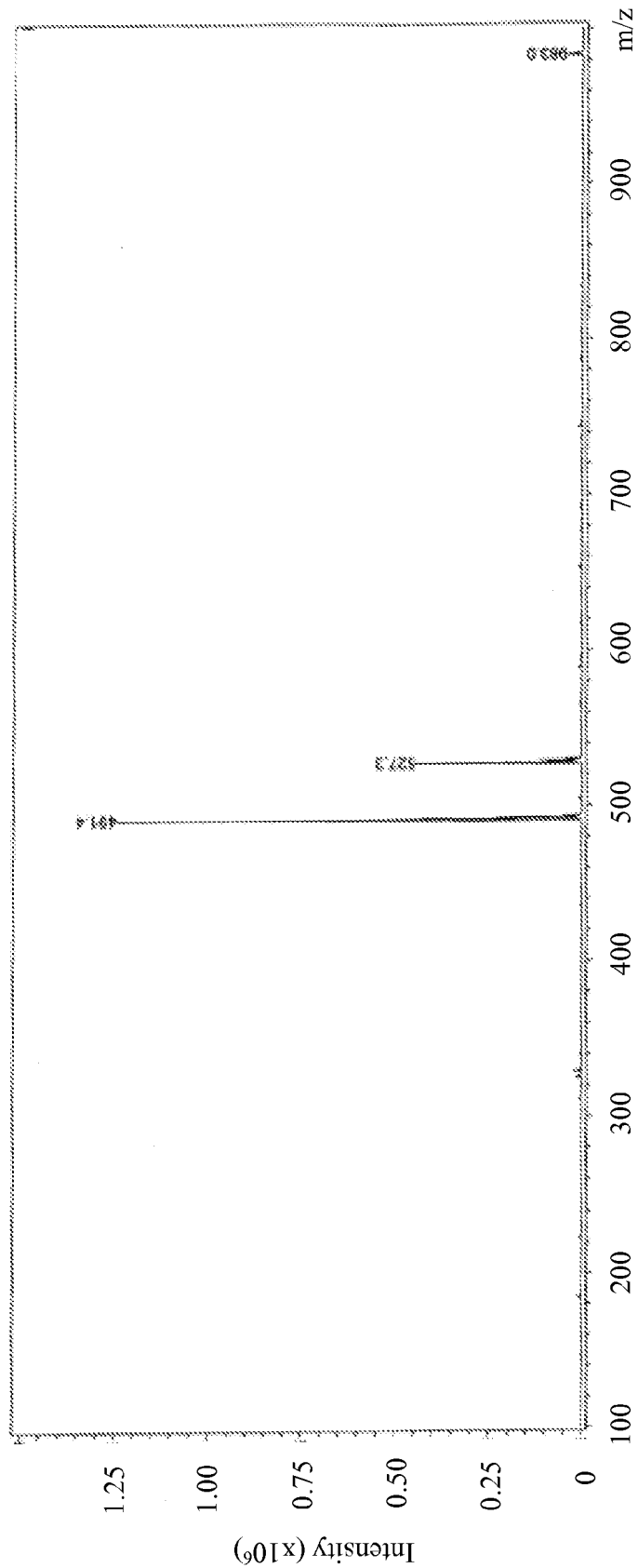
Figure 6A:
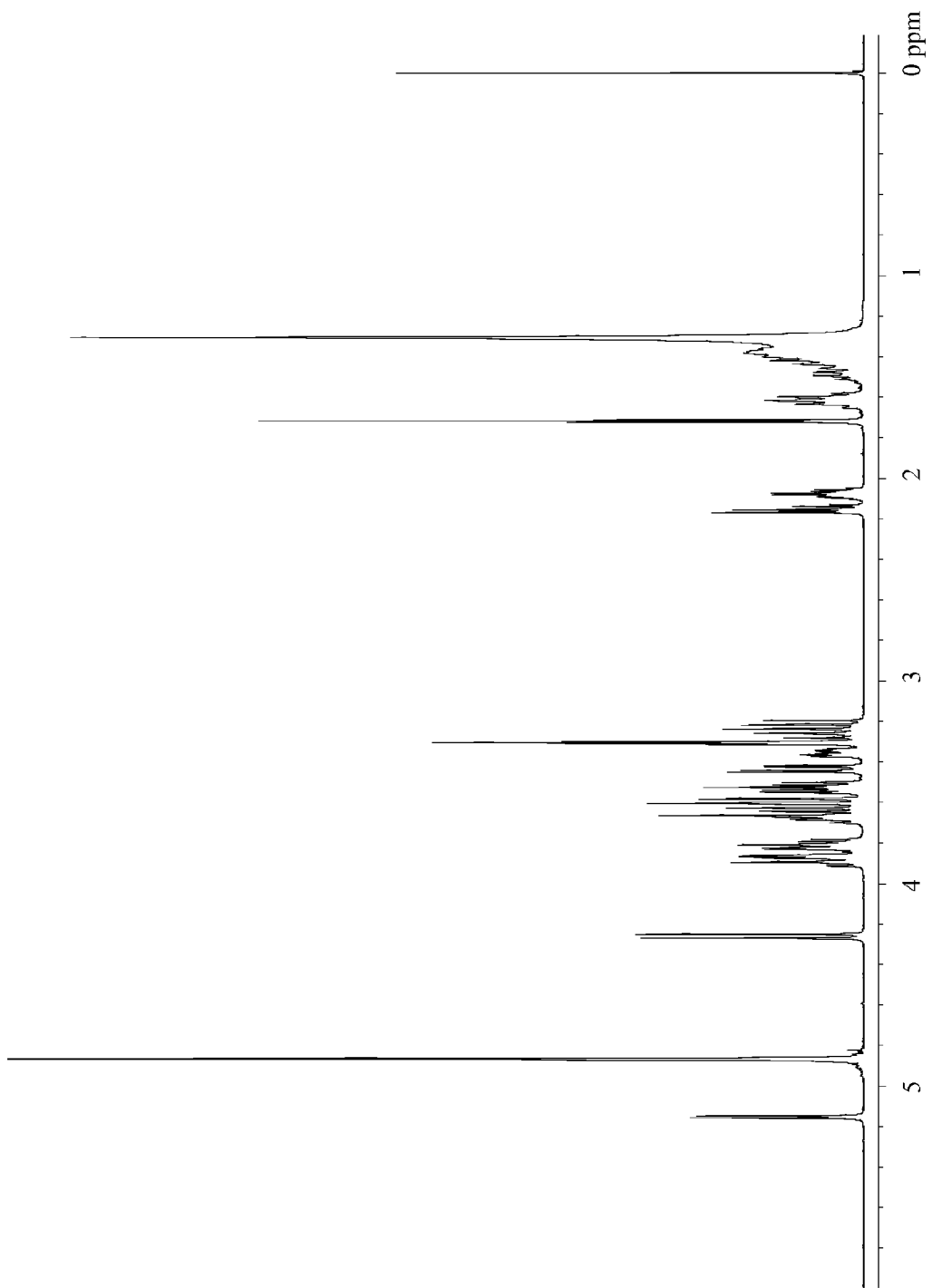
FIG. 6A-FIG. 6C are data obtained from $^1$H NMR, HPLC and MS analysis, respectively, of exemplary maltose alkyne derivative compound 12-tridecynyl-β-D-maltoside.
Figure 6B:
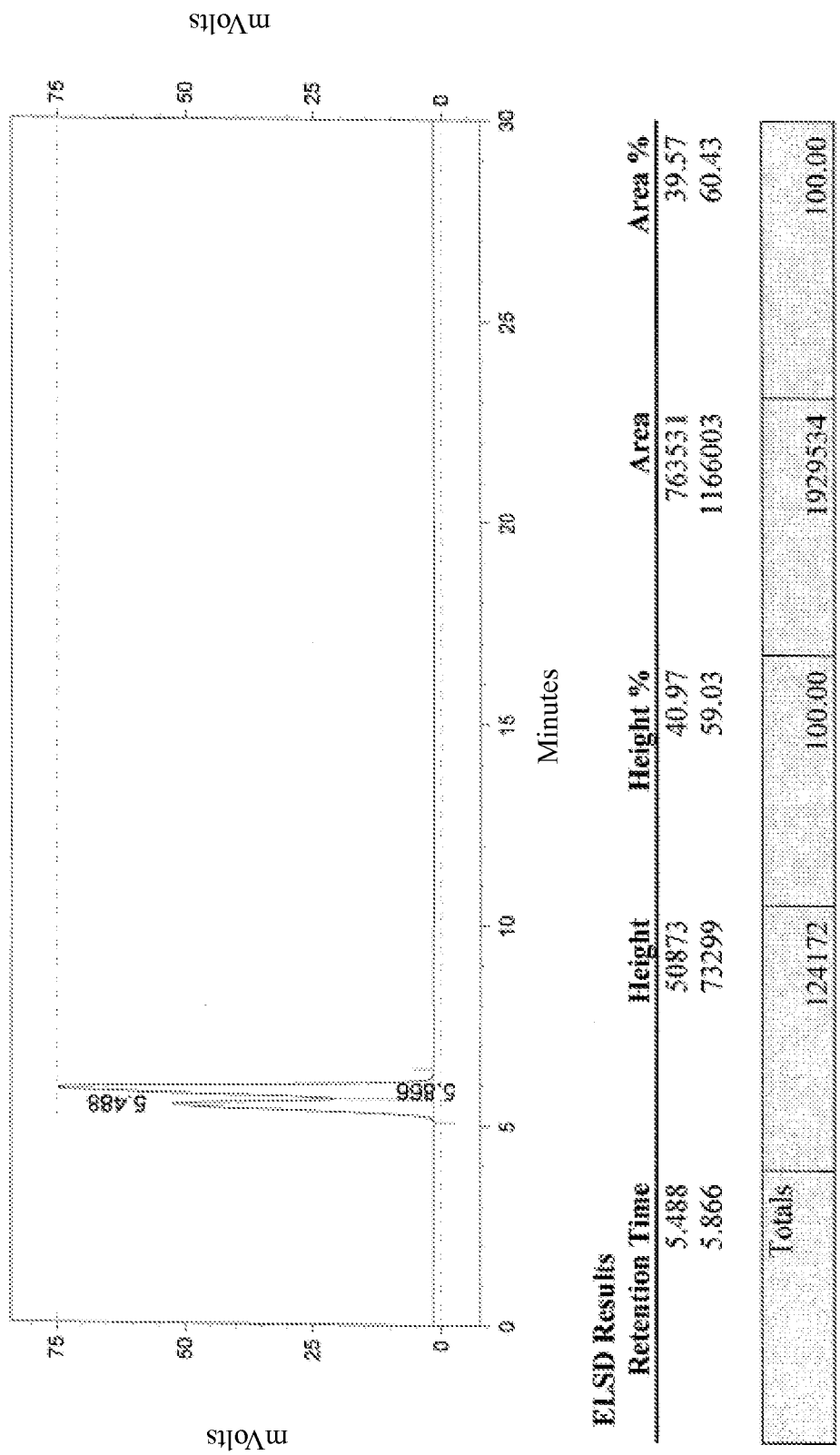
Figure 6C:
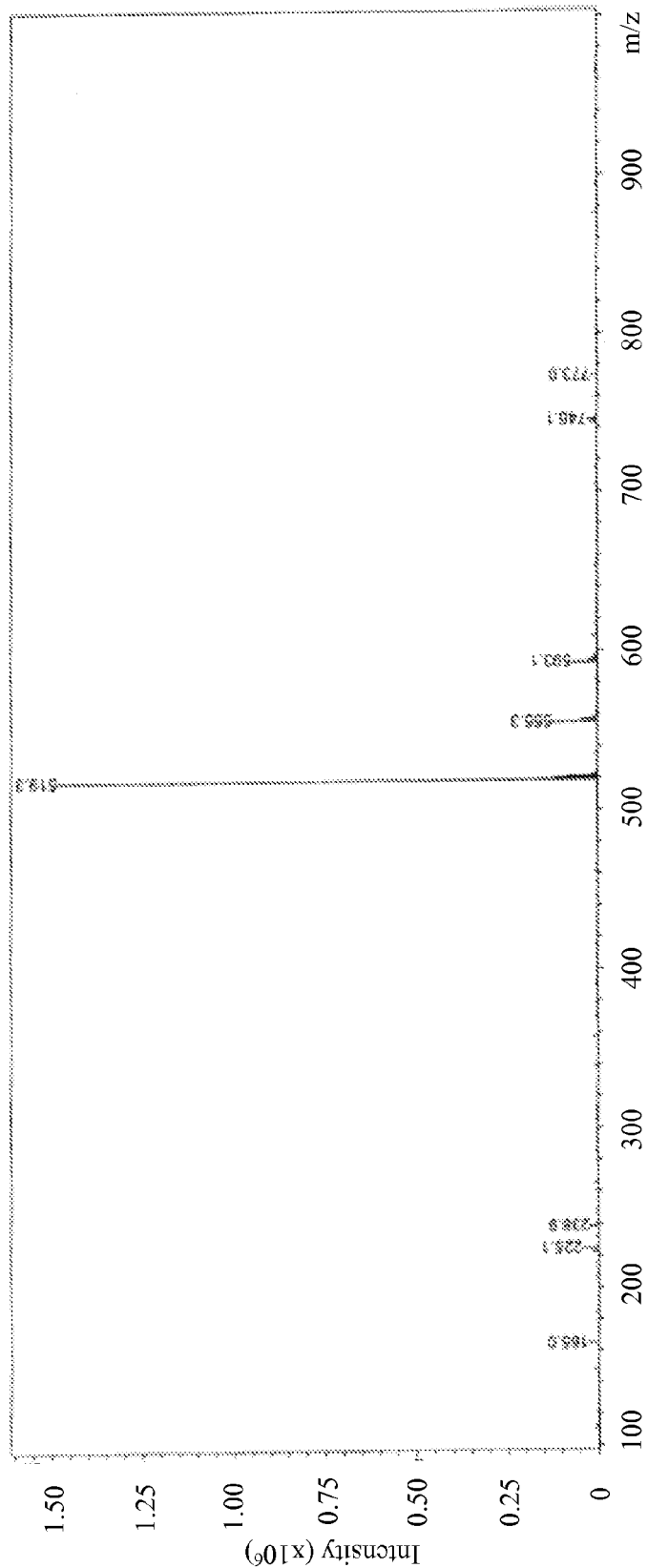
Figure 7A:
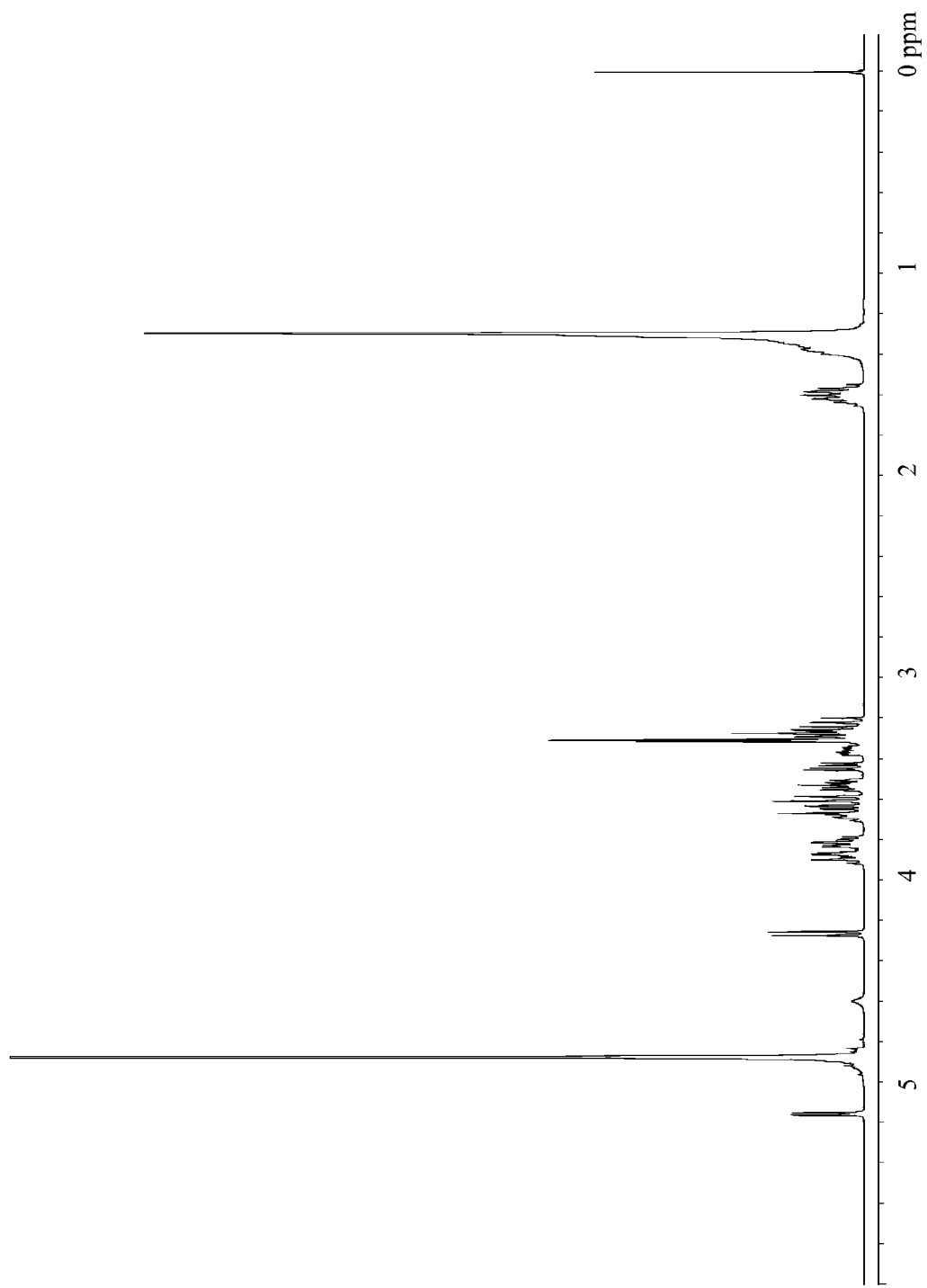
FIG. 7A-FIG. 7C are data obtained from $^1$H NMR, HPLC and MS analysis, respectively, of exemplary maltose azide derivative compound 16-azido-hexadecyl-β-D-maltoside.
Figure 7B:
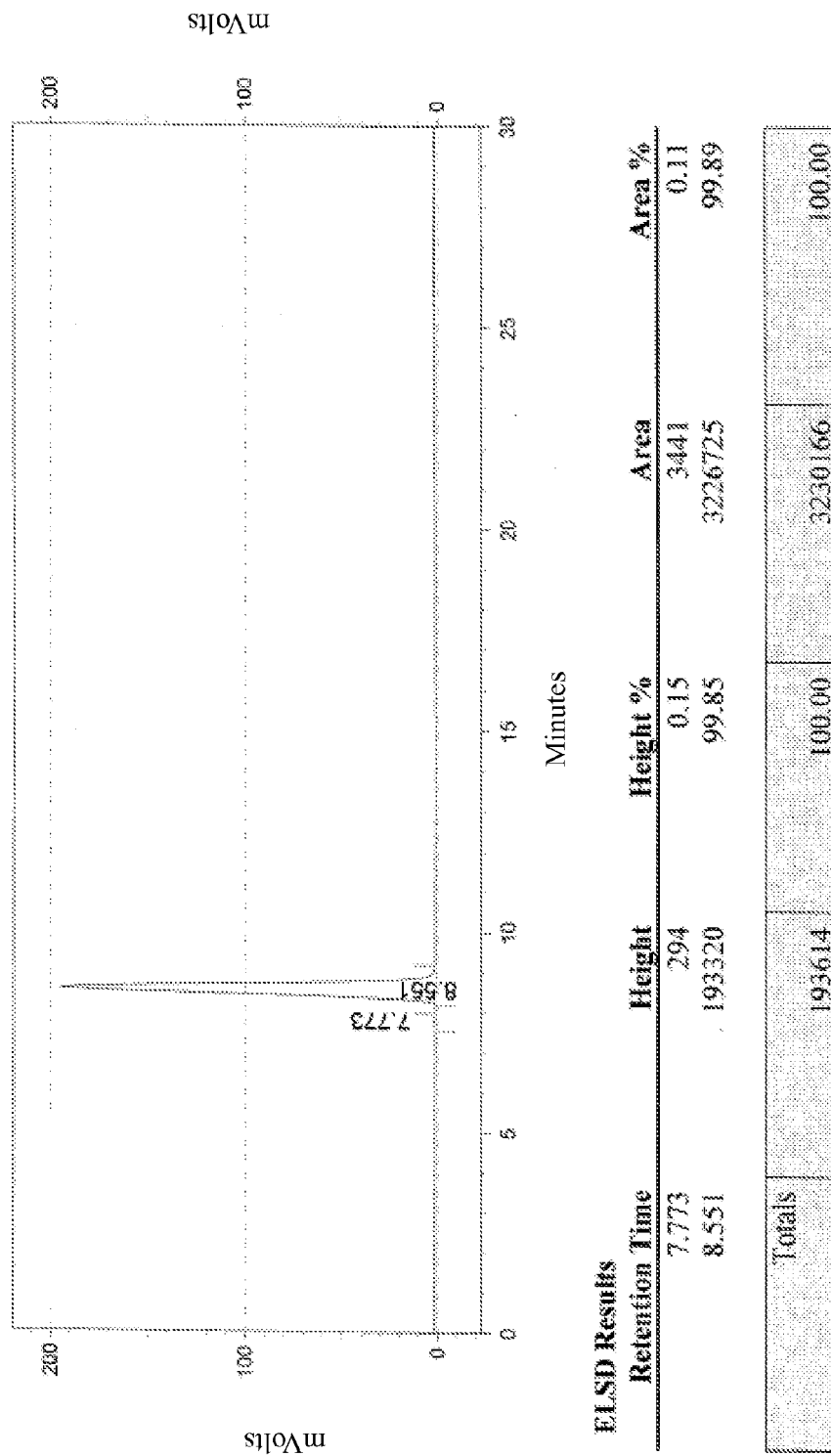
Figure 7C:
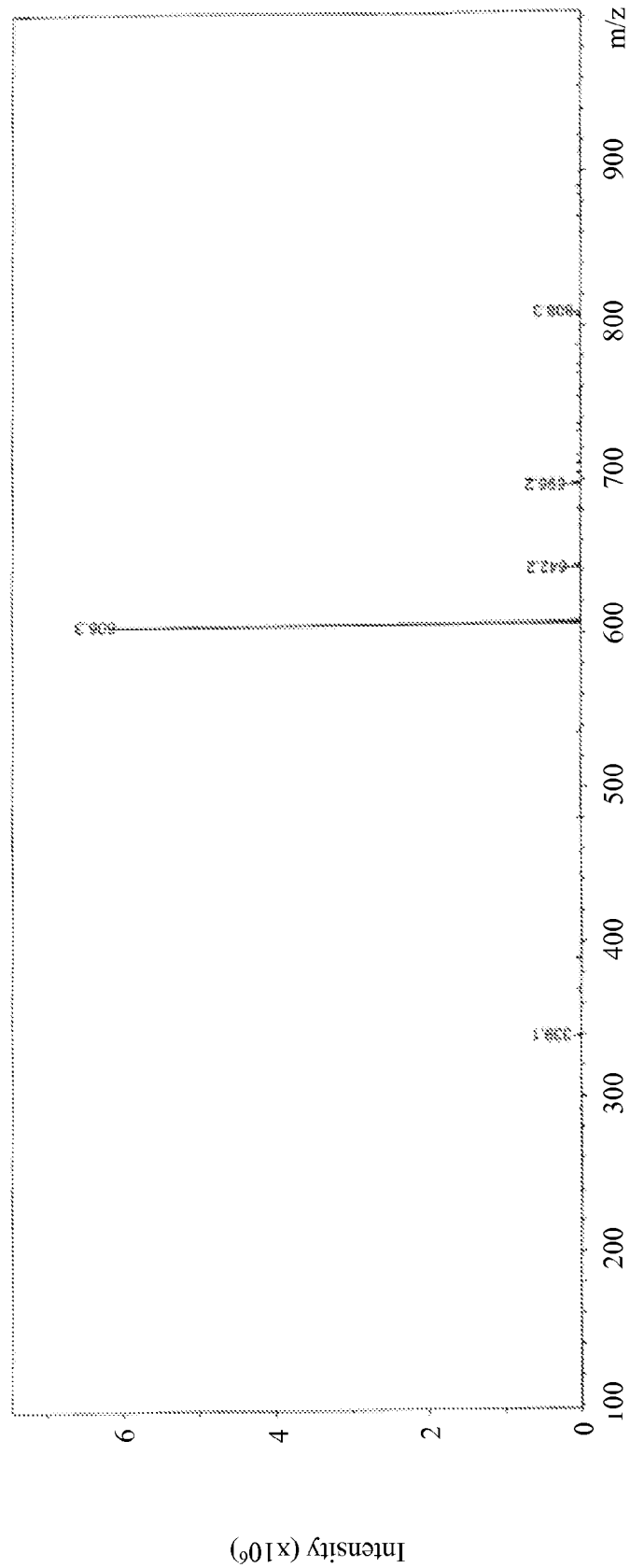
Figure 8A:
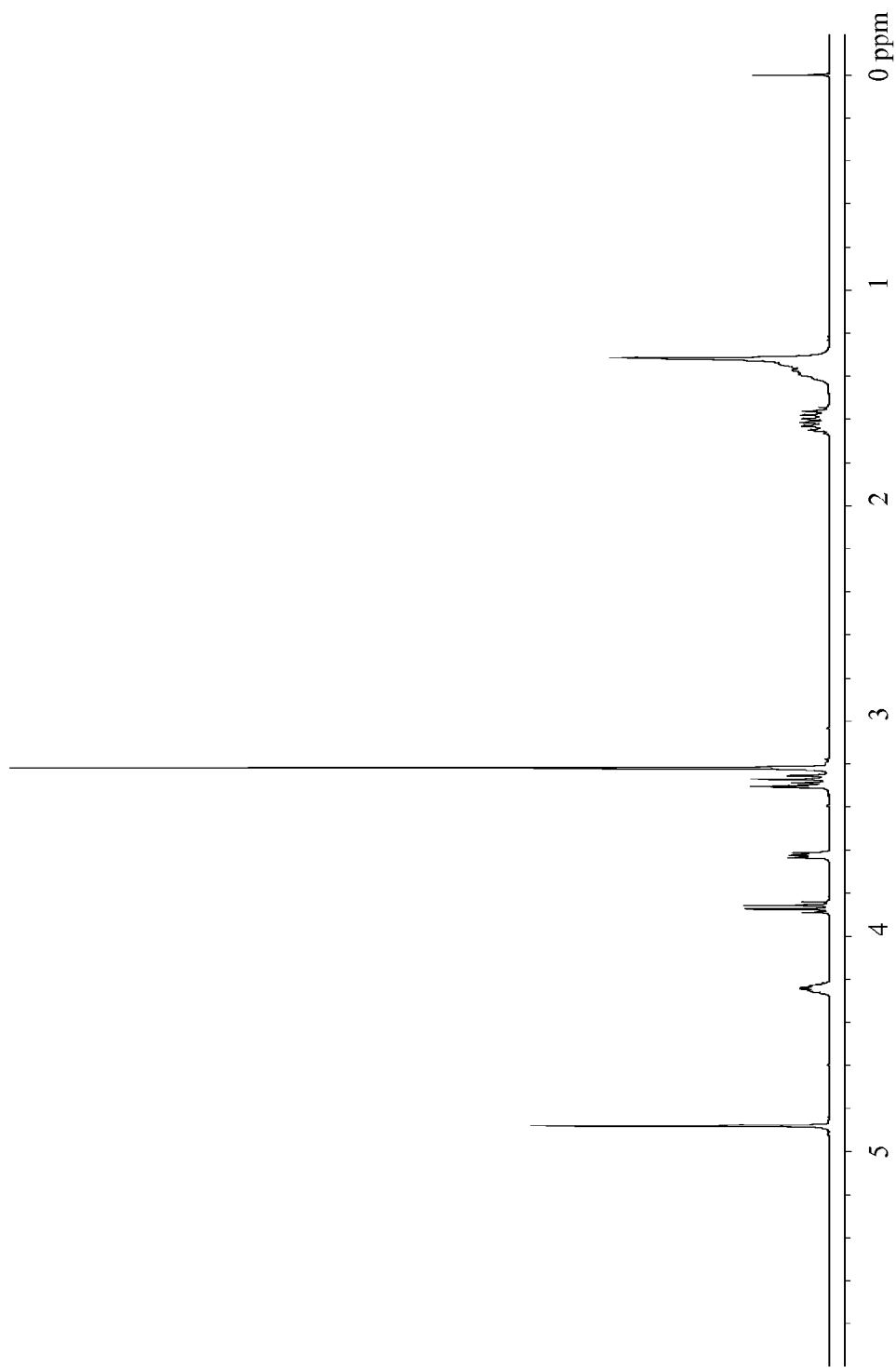
FIG. 8A-FIG. 8C are data obtained from $^1$H NMR, HPLC and MS analysis, respectively, of exemplary phosphocholine azido derivative compound 11-azido-undecyl-1-phosphocholine.
Figure 8B:
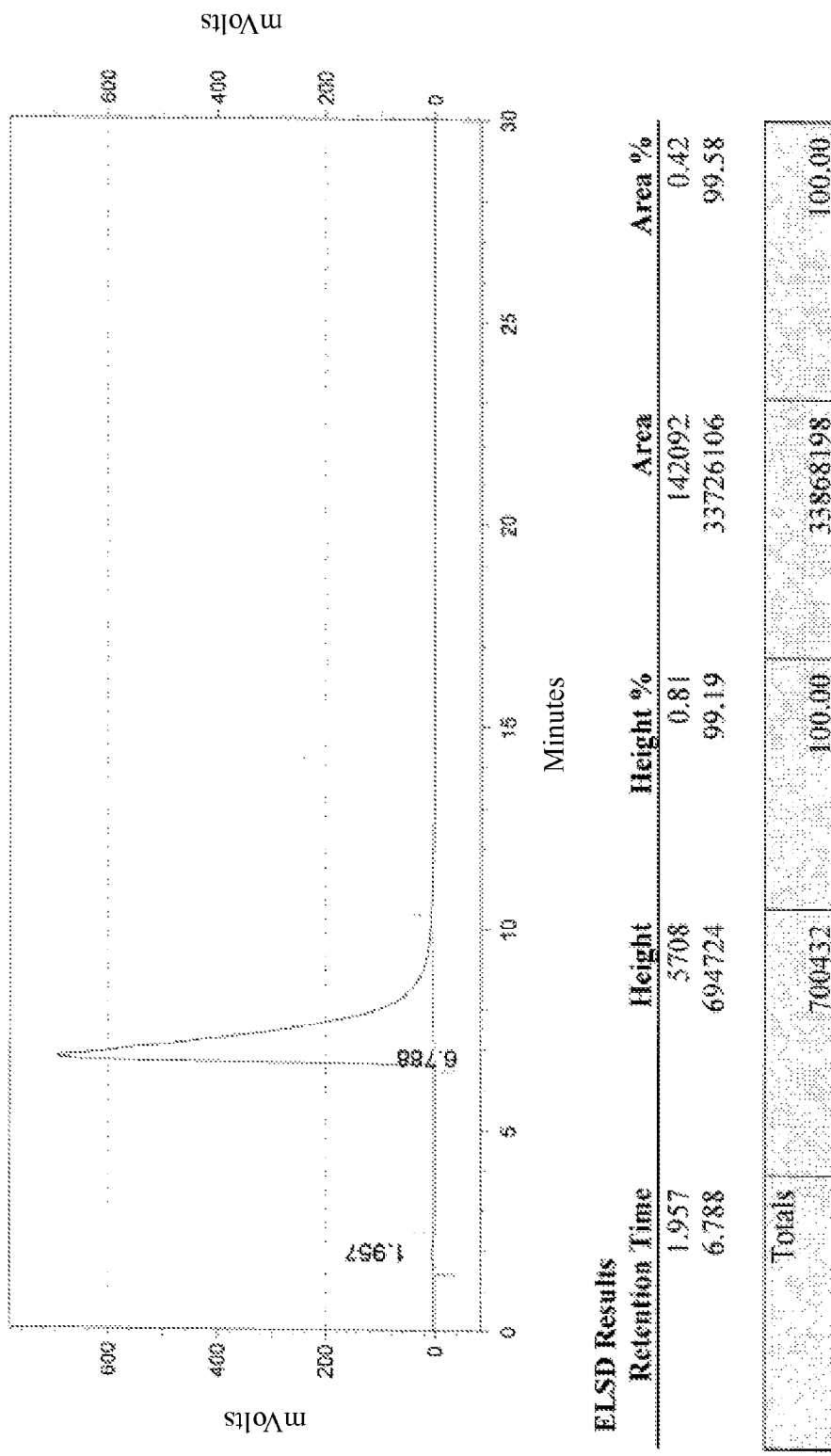
Figure 8C:
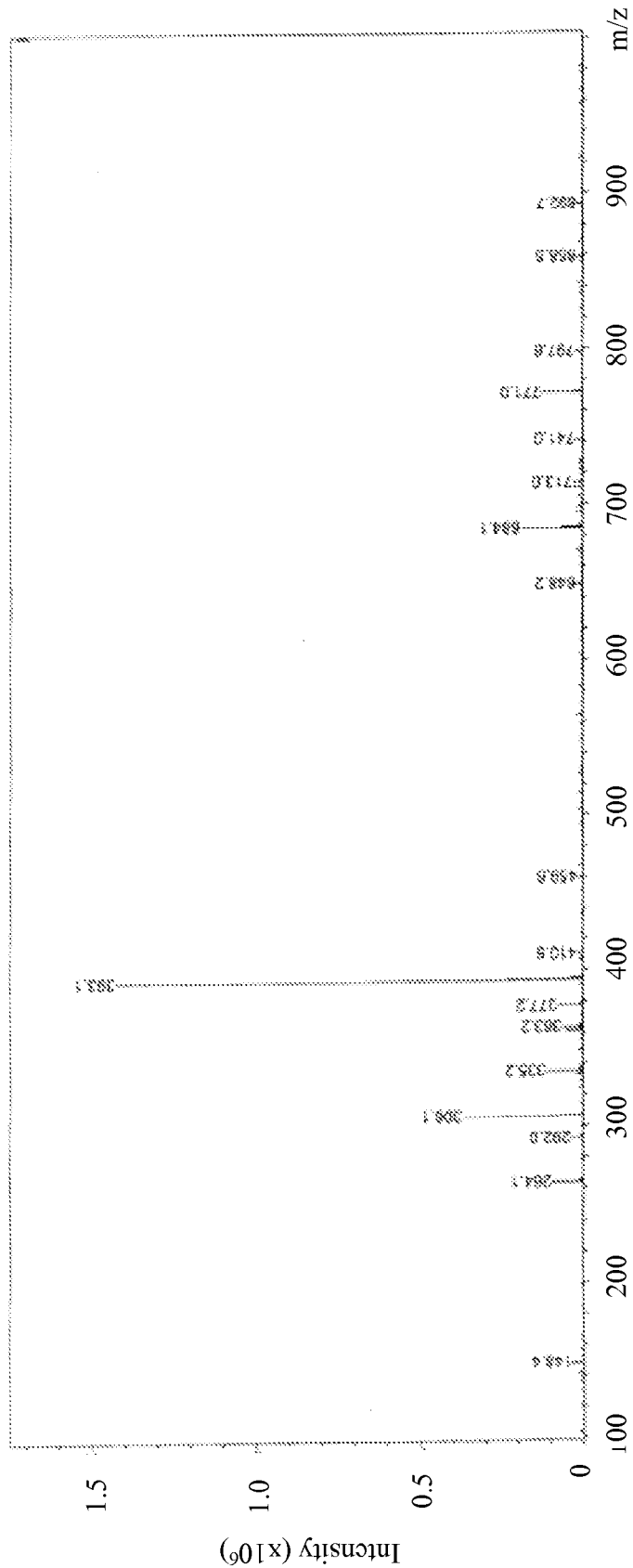
Figure 9A:
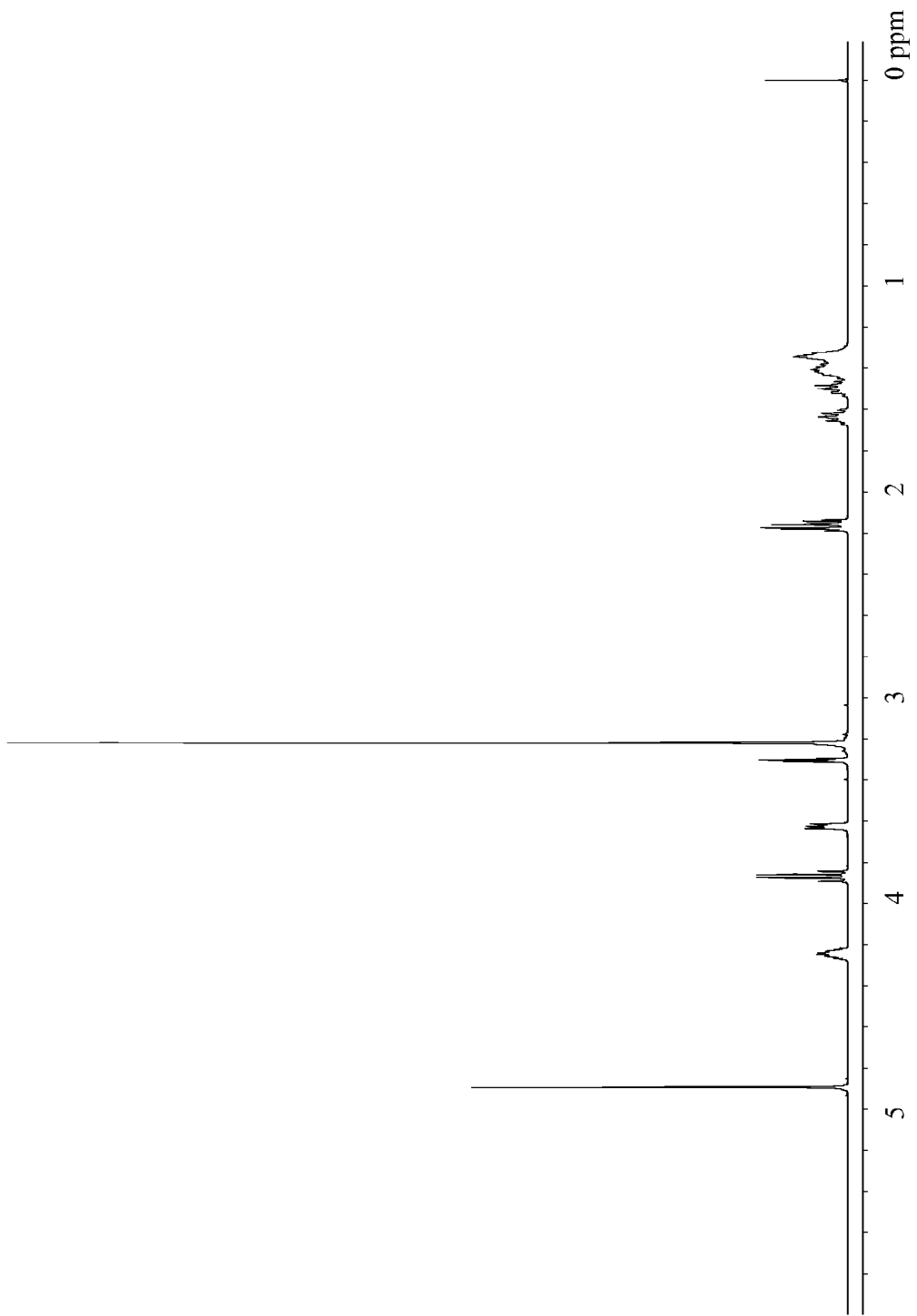
FIG. 9A-FIG. 9C are data obtained from $^1$H NMR, HPLC and MS analysis, respectively, of exemplary phosphocholine alkyne derivative compound 9-decynyl-1-phosphocholine.
Figure 9B:
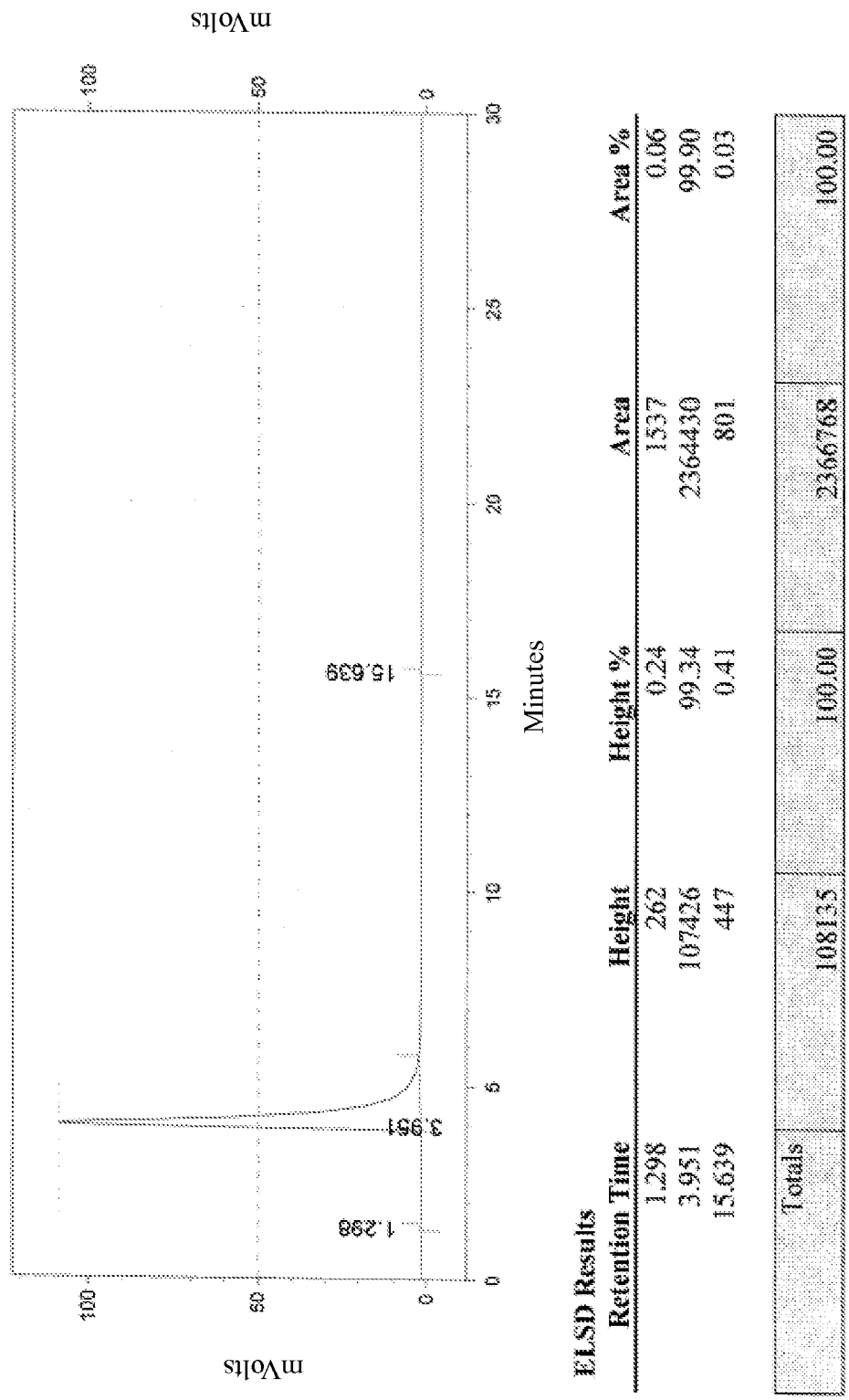
Figure 9C:
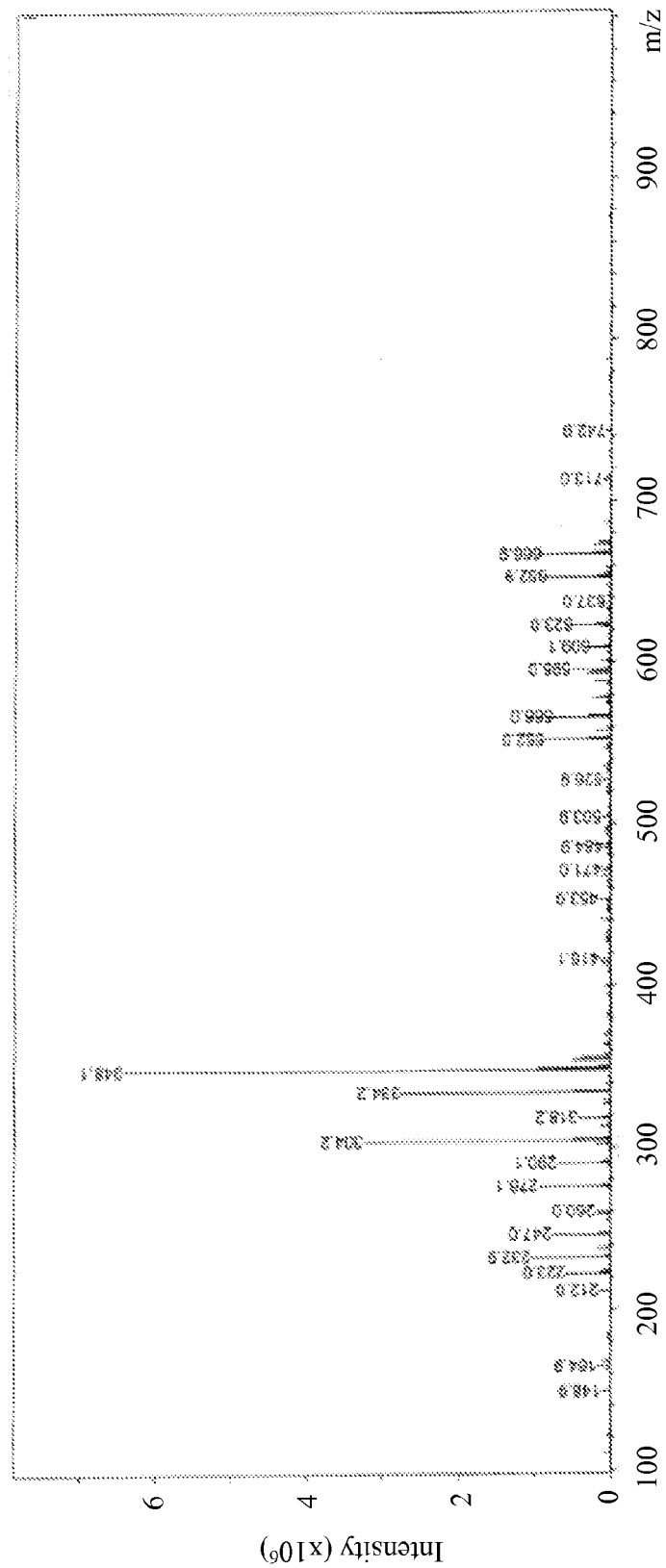
Figure 10A:
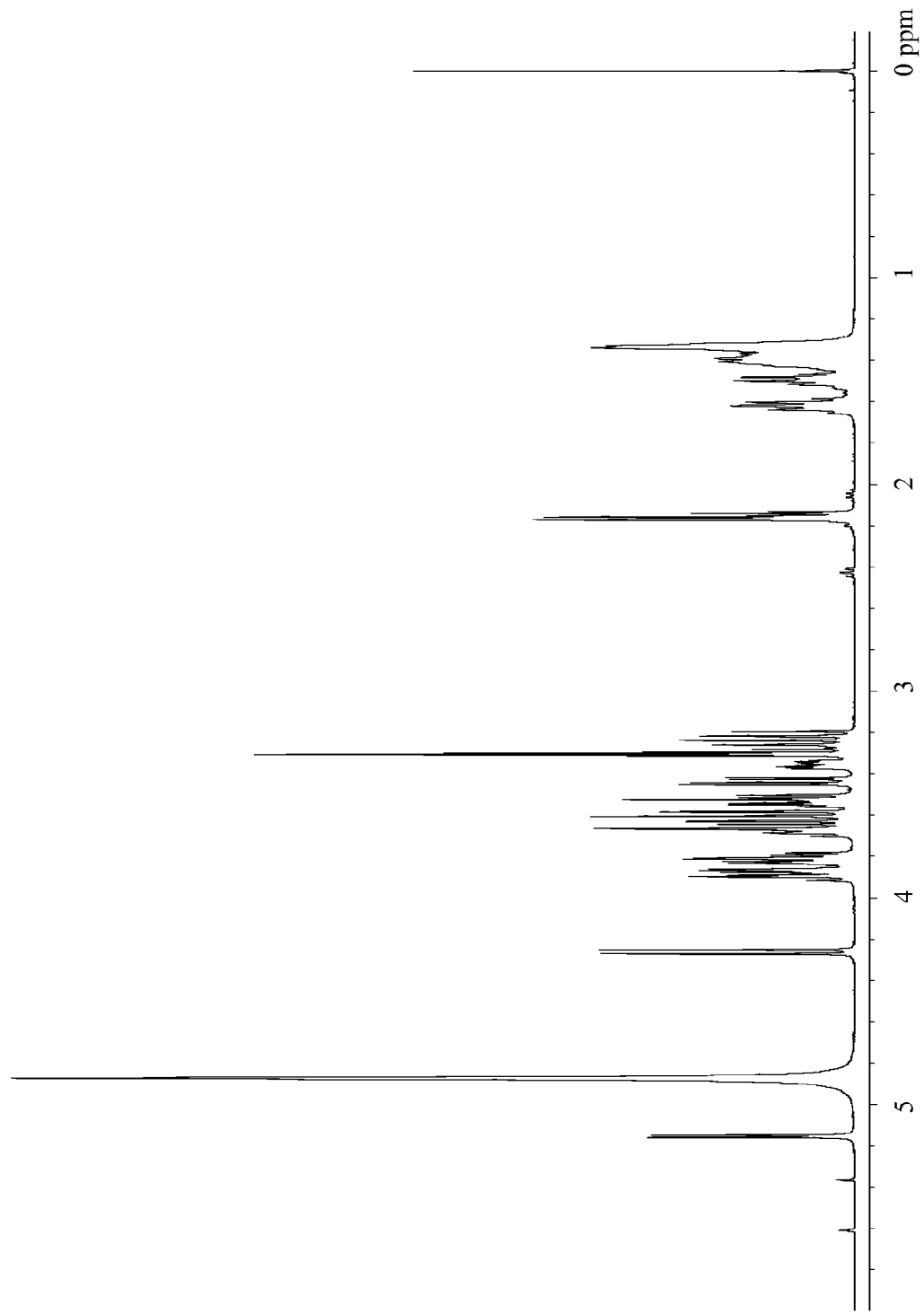
FIG. 10A-FIG. 10C are data obtained from $^1$H NMR, HPLC and MS analysis, respectively, of exemplary maltose alkyne derivative compound 9-decynyl-β-D-maltoside.
Figure 10B:
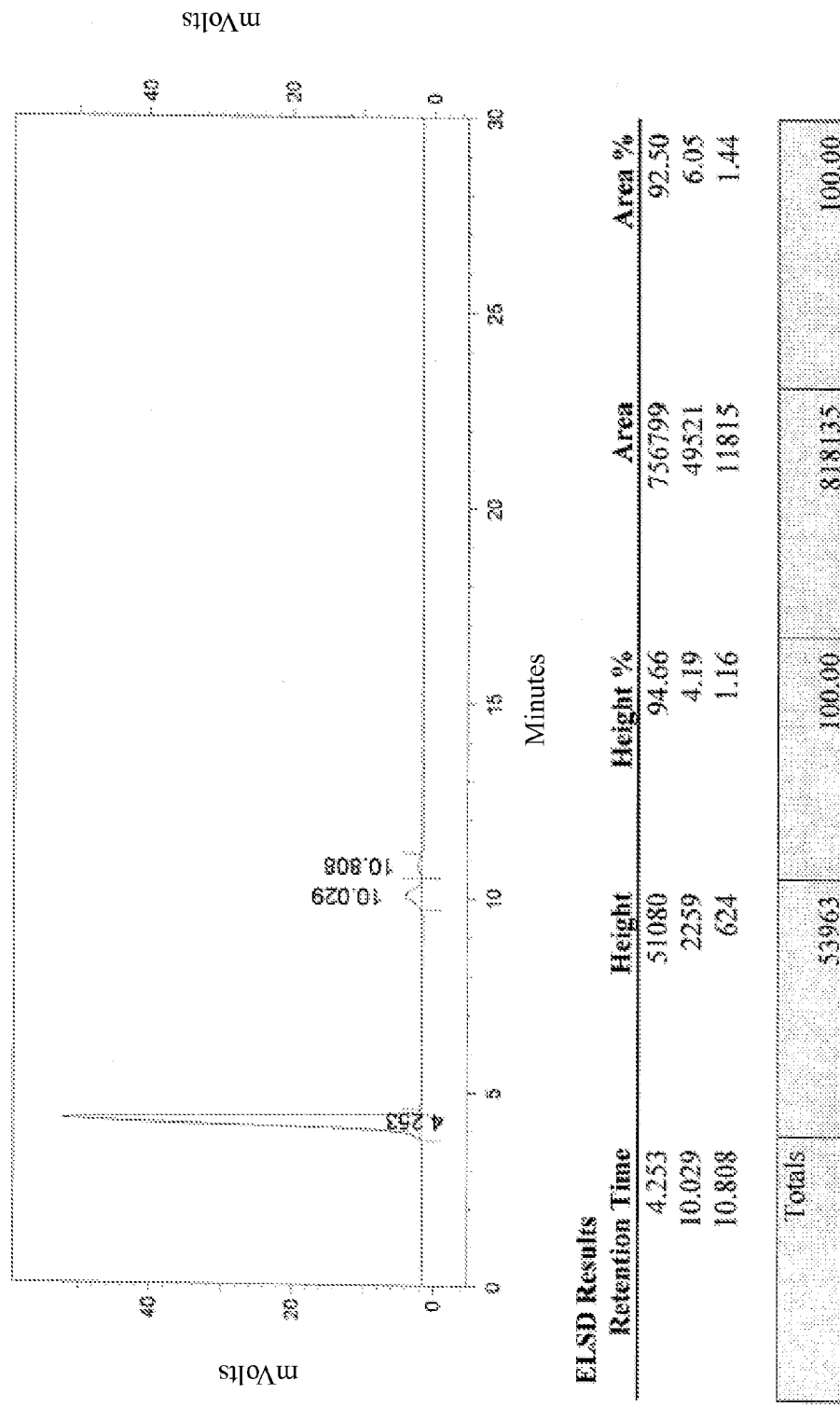
Figure 10C:
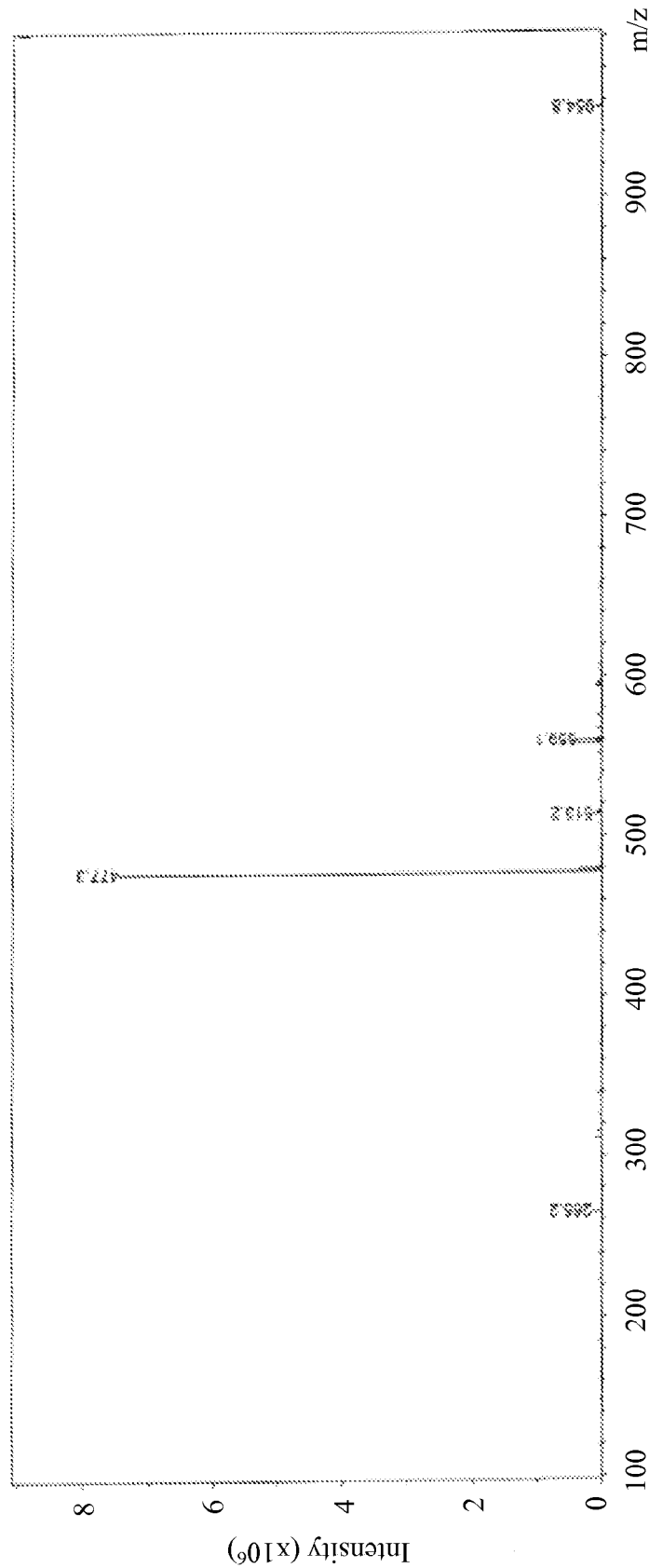

See FIGS. 4-10 for exemplary data comprising NMR and MS analysis of the synthesized compounds.

While the foregoing invention has been described in some detail for purposes of clarity and understanding, it will be clear to one skilled in the art from a reading of this disclosure that various changes in form and detail can be made without departing from the true scope of the invention. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A composition comprising:
an azide linked to a saccharide via a carbon chain having the formula:

wherein:
Az=azide,
Sac=saccharide selected from the group consisting of: trehalose, glucose and maltose,
n=7-20, and
wherein the carbon chain is covalently attached to an oxygen of an anomeric carbon of the saccharide.

2. The composition according to claim 1, wherein the saccharide is β-D-maltose.

3. The composition according to claim 2, wherein the azide linked to a saccharide via a carbon chain is 11-azido-undecyl-β-D-maltoside or 16-azido-hexadecyl-β-D-maltoside.

4. A composition comprising:
an alkyne linked to a saccharide via a carbon chain having the formula:

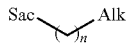

wherein:
Alk=C≡C—H
Sac=saccharide selected from the group consisting of: trehalose, glucose and maltose,
n=7-20, and
wherein the carbon chain is covalently attached to an oxygen of an anomeric carbon of the saccharide.

5. The composition according to claim 4, wherein the saccharide is β-D-maltose.

6. The composition according to claim 4, wherein the alkyne linked to a saccharide via a carbon chain is selected from the group consisting of: 9-decynyl-β-D-maltoside, 10-undecynyl-β-D-maltoside and 12-tridecynyl-β-D-maltoside.

7. A composition comprising:
an alkyne linked to phosphocholine via a carbon chain having the formula:

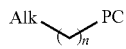

wherein:
Alk=H—C≡C
PC=phosphocholine, and
7≤n≤20.

8. The composition according to claim 7, wherein the alkyne linked to phosphocholine via a carbon chain is 9-decynyl-1-phosphocholine.

9. A composition comprising:
an azide linked to a saccharide via a first carbon chain having the formula:

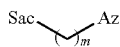

wherein:
Az=azide,
Sac=saccharide selected from the group consisting of: trehalose, glucose and maltose,
7≤m≤20, and
wherein the carbon chain is covalently attached to an oxygen of an anomeric carbon of the saccharide, and
an alkyne linked to phosphocholine via a second carbon chain according to:

wherein:
Alk=H—C≡C
PC=phosphocholine, and
7≤n≤20.

10. The composition according to claim 9, wherein the saccharide is maltose.

11. The composition according to claim 10, wherein the azide linked to a saccharide via a carbon chain is 11-azido-undecyl-β-D-maltoside or 16-azido-hexadecyl-β-D-maltoside, and wherein the alkyne linked to phosphocholine via a carbon chain is 9-decynyl-1-phosphocholine.

12. A composition comprising:
an azide linked to phosphocholine via a carbon chain having the formula:

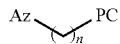

wherein:
Az=azide,
PC=phosphocholine, and
n=8-20.

13. The composition according to claim 12, wherein the azide linked to phosphocholine via a carbon chain is 11-azido-undecyl-1-phosphocholine.

14. A composition comprising a 1,4-disubstituted [1,2,3]-triazole formed from the reaction of:
an alkyne linked to a saccharide via a first carbon chain having the formula:

wherein:
Alk=C≡C—H
Sac=saccharide selected from the group consisting of: trehalose, glucose and maltose,
7≤m≤20, and
wherein the carbon chain is covalently attached to an oxygen of an anomeric carbon of the saccharide, and
an azide linked to phosphocholine via a second carbon chain having the formula:

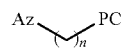

wherein:
Az=azide,
PC=phosphocholine, and
7≤n≤20.

15. The composition according to claim 14, wherein the saccharide is maltose.

16. A method of forming a micelle or lipid bilayer, which comprises:
(A) reacting an alkyne linked to a saccharide via a first carbon chain having the formula:

wherein:
Alk=C≡C—H
Sac=saccharide selected from the group consisting of: trehalose, glucose and maltose,
7≤m≤20, and
wherein the carbon chain is covalently attached to an oxygen of an anomeric carbon of the saccharide,
with
an azide linked to phosphocholine via a second carbon chain having the formula:

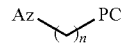

wherein:
Az=azide,
PC=phosphocholine, and
7≤n≤20,
under conditions which form a 1,4-disubstitued [1,2,3]-triazole; and
incubating the 1,4-disubstitued [1,2,3]-triazole under conditions conducive to formation of a micelle or lipid bilayer,
or
(B) reacting an azide linked to a saccharide via a first carbon chain having the formula:

wherein:
Az=azide,
Sac=saccharide selected from the group consisting of: trehalose, glucose and maltose,
7≤m≤20, and
wherein the carbon chain is covalently attached to an oxygen of an anomeric carbon of the saccharide,
with
an alkyne linked to phosphocholine via a second carbon chain having the formula:

wherein:
Alk=H—C≡C
PC=phosphocholine, and
7≤n≤20
under conditions which form a 1,4-disubstitued [1,2,3]-triazole; and
incubating a sufficient quantity of the 1,4-disubstitued [1,2,3]-triazole under conditions conducive to formation of a micelle or lipid bilayer.

17. The method according to claim 16, wherein the saccharide is a maltose.

18. The method according claim 16, further comprising:
mixing a sufficient quantity of the 1,4-disubstituted [1,2,3]-triazole from step (A) with the 1,4-disubstituted [1,2,3]-triazole from step (B); and
incubating the mixture under conditions conducive to formation of a micelle or lipid bilayer.

\* \* \* \* \*